United States Patent
Zagumennyi et al.

(10) Patent No.: US 7,132,060 B2
(45) Date of Patent: Nov. 7, 2006

(54) SCINTILLATION SUBSTANCES (VARIANTS)

(75) Inventors: Alexander Iosifovich Zagumennyi, Moscow (RU); Yuri Dmitrievich Zavartsev, Moscow (RU); Sergei Alexandrovich Kutovoi, Moscow (RU)

(73) Assignee: Zecotek Medical Systems Inc.

( * ) Notice: Subject to any disclaimer, the term of this patent is extended or adjusted under 35 U.S.C. 154(b) by 0 days.

(21) Appl. No.: 10/502,960

(22) PCT Filed: Mar. 12, 2004

(86) PCT No.: PCT/RU2004/000094

§ 371 (c)(1),
(2), (4) Date: Jul. 21, 2005

(87) PCT Pub. No.: WO2005/042812

PCT Pub. Date: May 12, 2005

(65) Prior Publication Data

US 2006/0086311 A1    Apr. 27, 2006

(51) Int. Cl.
| | |
|---|---|
| C30B 29/34 | (2006.01) |
| C30B 11/00 | (2006.01) |
| C30B 15/00 | (2006.01) |
| C30B 17/00 | (2006.01) |
| C30B 28/06 | (2006.01) |
| C30B 28/10 | (2006.01) |
| C09K 11/79 | (2006.01) |
| C04B 35/16 | (2006.01) |
| G01T 1/202 | (2006.01) |
| A61B 6/03 | (2006.01) |

(52) U.S. Cl. ............... 252/301.4 F; 117/13; 117/942
(58) Field of Classification Search ............... None
See application file for complete search history.

(56) References Cited

U.S. PATENT DOCUMENTS

| | | | |
|---|---|---|---|
| 4,647,781 | A | 3/1987 | Takagi .................. 250/361 R |
| 4,958,080 | A | 9/1990 | Melcher .................. 250/269 |
| 4,988,882 | A * | 1/1991 | Francois et al. ......... 250/483.1 |
| 5,660,627 | A | 8/1997 | Manente et al. ............. 117/12 |
| 6,278,832 | B1 | 8/2001 | Zagumennyi et al. ....... 385/141 |

(Continued)

OTHER PUBLICATIONS

K.T. Wilke "A growing of crystals" Leningrad, publisher<Nedra>, (1977), 600p., a translation from Geramn von K. Th. Wilke "Kristallzuchtungen"<VEB Deutcher Verlag der Wissenschaften, Berlin, 1973.*

(Continued)

*Primary Examiner*—C. Melissa Koslow
(74) *Attorney, Agent, or Firm*—Thomas E. Loop

(57) ABSTRACT

Inventions relates to scintillation substances and they may be utilized in nuclear physics, medicine and oil industry for recording and measurements of X-ray, gamma-ray and alpha-ray, nondestructive testing of solid states structure, three-dimensional positron-emission tomography and X-ray tomography and fluorography. Substances based on silicate comprising lutetium and cerium characterized in that compositions of substances are represented by chemical formulae $Ce_xLu_{2+2y-x}Si_{1-y}O_{5+y}$, $Ce_xLi_{q+p}Lu_{2-p+2-y-x-z}A_zSi_{1-y}O_{5+y-p}$, $Ce_xLi_{q+p}Lu_{9.33-x-p-z}\square_{0.67}A_zSi_6O_{26-p}$, where A is at least one element selected from group consisting of Gd, Sc, Y, La, Eu, Tb, x is value between $1\times10^{-4}$ f.units and 0.02 f.units., y is value between 0.024 f.units and 0.09 f.units, z is value does not exceeding 0.05 f.units, q is value does not exceeding 0.2 f.units, p is value does not exceeding 0.05 f.units. Achievable technical result is the scintillating substance having high density, high light yield, low afterglow, and low percentage loss during fabrication of scintillating elements.

20 Claims, 3 Drawing Sheets

U.S. PATENT DOCUMENTS

| | | | |
|---|---|---|---|
| 6,323,489 B1 | 11/2001 | McClellan et al. | 250/361 R |
| 6,413,311 B1 | 7/2002 | Melcher et al. | 117/13 |
| 6,437,336 B1 | 8/2002 | Pauwels et al. | 250/361 R |
| 6,464,777 B1 | 10/2002 | Kitamura et al. | 117/13 |
| 6,498,828 B1 | 12/2002 | Jiang et al. | 250/483.1 |
| 6,753,099 B1* | 6/2004 | Imamura et al. | 428/690 |
| 2005/0173676 A1* | 8/2005 | Kurashige et al. | 252/301.4 F |

OTHER PUBLICATIONS

A.A. Vershman, K.I. Petrov, "A functional inorganic lithium compound" Moscow, Energoizdat, (1996), 208p.*

P.I. Antonov, L.M. Zatulovski, A.S. Kostygov et al., "An obtaining of profiled single crystals and products by Stepanov's method", Leningrad, "Nauka", (1981) p. 280.*

Carel W.E. van Eijk "Inorganic scintillators in medical imaging detectors", Nuclear Instruments and Methods in Physics Research A 509 (2003) pp. 17-25.

A.G. Gomes, A.Bril "Preparation and Cathodoluminescence of Ce3+ activated yttrium silicates and some isostructural compounds", Mat. Res. Bull. vol. 4, (1969) pp. 643-650.

W.Rossner, R.Breu "Luminescence properties cerium-doped gadolinium oxyorthosilicate cera-mics scintillators" Proc. Int. Conf. on Inorganic Scintillators and Their Application, STINT'95, Netherlands, Delft University, (1996) p. 376-379.

P.Dorenbost, C. van Eijekt, A.Bost, C.Melcher "Afterglow and thermoluminescence properties of Lu2SiO5:Ce scintillation crystals", J.Phys.Condens.Matter 6 (1994), pp. 4167-4180.

M.E. Globus, B.V. Grinev "Inorganic scintillators", publishing house 'AKTA' Kharkov, (2000) p. 51.

W.M. Moses, S.E. Derenzo "Scintillators for positron emission tomography", Conference SCINT'95, Delft, The Netherlands (1995), LBL-37720.

A.M.Korovkin, T.I.Merkulyaeva, L.G.Morozova, I.A.Pechanskaya, M.V.Petrov, I.R.Savinova "Optical and spectral-luminescence properties of the orthosilicate crystals of lanthanide" Optics and Spectroscopy, value 58, issue 6 (1985) p. 1266-1269.

I.A. Bondar, N.V. Vinogradova, L.N. Dem'yanets et al. "Silicates, germanates, phosphates, arsenates, and vanadates. Chemistry of rare elements" monograph, Moscow, Nauka, (1983) 288 p.

The international X-ray library's database, PDF Database, International Center for Diffraction Data, Newton Square, PA, U.S.A.

R.L. Byer, J.F. Young "Growth of High-Quality LiNbO3 Crystals from the Congruent Melt" Journal of Appl. Phys. 41, N6, (1970), p. 2320-2325.

P. Lerner, C. Legras, J. Dumas "Stoechiometrie des mohocristaux de metaniobate de lithium", Journal of Crystal Growth, 3,4 (1968) p. 231-235.

P.V. Geld, F.A. Sidorenko "Dependence of physical-chemical properties of non-stoichiometric compounds on structure of short-range order" Izvestia AN SSSR, seria Inorganic materials, v.15, #6, (1979) p. 1042-1048.

D.T.J. Hurle "Crystal Pulling from the Melt" Springer-Verlag, Berlin, Heidelberg, New-York, London, Paris, Tokyo, Hong Kong, Budapest, (1993) p. 21.

C.D. Brandle, A.J.Valentino, G.W.Berkstresser "Czochralski growth of rare-earth orthosilicates (Ln2SiO5)", J. Crystal Growth 79 (1986), pp. 308-315.

E.G. Devitsin, V.A. Kozlov, S.Yu Potashov, A.I. Zagumennyi, Yu.D. Zavartsev "Luminescent properties of Lu3A15O12 crystal doped with Ce" Proceeding of International Conferences "Inorganic scintillators and their applications" (SCINT 95), Delft, the Netherlands, Aug. 20-Sep. 1, (1995).

* cited by examiner

SCINTILLATION SUBSTANCES (VARIANTS)

BACKGROUND OF THE INVENTION

The invention is applied to scintillation materials and may be used in nuclear physics, medicine, and oil industry for recording and measuring of X-ray, gamma- and alpha-radiation; non-destructive testing of solid state structure; three-dimensional positron-electron computer tomography (PET) and X-ray computer fluorography. The relevance of the invention is that in fluoroscopy, X-ray computer tomography and PET, an introduction of new/improved scintillators has resulted in significant improvement of the image quality or/and reduced the measuring time. ("Inorganic scintillators in medical imaging detectors" Carel W. E. van Eijk, Nuclear Instruments and Methods in Physics Research A 509 (2003) 17–25).

The known scintillation substance is a lutetium oxyorthosilicate powder doped with cerium $Lu_{1.98}Ce_{0.02}SiO_5$ (A. G. Gomes, A. Bril "Preparation and Cathodoluminescence of $Ce^{3+}$ activated yttrium silicates and some isostructural compounds", Mat. Res. Bull. Vol. 4, 1969, pp. 643–650). This phosphor was created for an application in the cathodoluminescence devices, however this substance may be utilized also for the X-ray, gamma- and alpha-ray emissions recording.

It is known the scintillation substance/crystal of cerium doped lutetium oxyorthosilicate $Ce_{2x}Lu_{2(1-x)}SiO_5$, where x is varied between the limits from $2 \times 10^{-4}$ to $3 \times 10^{-2}$ (U.S. Pat. No. 4,958,080, Sep. 18, 1990). The crystals of this composition are grown from a melt having composition of $Ce_{2x}Lu_{2(1-x)}SiO_5$. In scientific literature abbreviated name LSO:Ce is wide used for denotation of this crystal. The $Ce_{2x}Lu_{2(1-x)}SiO_5$ scintillation crystals have a number of advantages in comparison with other crystals: a high density, a high atomic number, relatively low refractive index, a high light yield, a short decay time of scintillation. The disadvantage of known scintillation material is the large spread of important characteristics of scintillation, namely, a light yield and an energy resolution, from crystal to crystal. The experimental results of systematic measurements of commercially produced LSO:Ce crystals grown by CTI Inc. company (Knoxville, USA) clearly display this (U.S. Pat. No. 6,413,311, Jul. 2, 2002). Another disadvantage is a significant reduction of light yield, when the containing LSO:Ce crystal device is operated under conditions when the temperature is above a room temperature, for example, in petroleum industry for the rock composition analyses in a borehole during the search of the new deposits. Another disadvantage of LSO:Ce crystals is an afterglow effect, that is the prolonging fluorescence after radiation exposure, for example, the luminescence intensity of the samples described in U.S. Pat. No. 4,958,080 is reduced to decibels during ten minutes.

It is known the scintillation substance the lutetium oxyorthosilicate containing cerium, $Ce:Lu_2SiO_5$, in the form of a transparent ceramics. The $Lu_2SiO_5:Ce$ scintillator is formed into ceramics material through sintering the $Lu_2SiO_5:Ce$ powder. Because the $Lu_2SiO_5:Ce$ has a monoclinic structure rather than a cubic crystalline structure, the sintering produces a translucent ceramics rather than transparent. The cerium-doped lutetium orthosilicate is formed into a transparent glass scintillator by combining the silicate oxide, lutetium oxide, cerium oxide, potassium oxide, and barium oxide. The pores between the particles are removed which results in a consolidation of the scintillator material. As a result, the translucent ceramics is converted into a transparent ceramics applicable for using in the medicine tomographs (U.S. Pat. No. 6,498,828 from Dec. 12, 2002). The drawback of patent proposed is a quality of scintillation ceramics, which is made from, so-named, stoichiometric composition of lutetium oxyorthosi-licate mixture, a stoichiometric composition is characterised by ratio of formula units of (Lu+Ce)/Si is equal exactly to 2/1. Since the congruent composition of lutetium oxyorthosilicate does not coincide with stoichiometric one, the ceramics of stoichiometric composition apparently contains the components of oxides which did not react completely as a results the scattering centers are formed. The light yield is an important characteristic of a scintillator. The presence of scattering centers reduces a light yield appreci-ably. A transparent ceramics made from a cerium-doped gadolinium oxyorthosilicate has the same limi-tation (W. Rossner, R. Breu "Luminescence properties cerium-doped gadolinium oxyorthosilicate ceramics scintillators" Proc. Int. Conf. on Inorganic Scintillators and Their Application, STINT'95, Netherlands, Delft University, 1996, p. 376–379). The scintillation elements fabricated from the transparent ceramics have the 60% less light yield than the elements fabricated from the $Ce:Gd_2SiO_5$ crystals.

Presence of an afterglow is very unwanted effect for some applications, for example, for an imaging system, in which the electronic part of device indicates a photon flux from the scintillation elements absorbing the gamma radiation. The afterglow effect, i.e. a photon flux from the scintillation element does not exposed to gamma radiation, reduces a contrast range, a sensitivity and a precision of device. The afterglow impairs also the parameters of medical devices based on the utilization of positron emitting isotopes, for example, the three-dimensional medical tomographs (Fully-3D PET camera) for diagnostic of the cancer diseases, and, especially, for the MicroPET systems designed for testing of the new medicines. A principle of operation of the three-dimensional medical tomographs is that the microscopic concentration of substance containing an emitting positron isotope is introduced into the blood of a patient. This substance is accumulated in the cancer cells of patient. An emitted positron annihilates instantly with an electron this results in the emission of the two 511 KeV energy gamma-quantums scattering exactly in opposite directions. In tomograph the detection of both gamma-quantums occurs by means of the several ring detectors each of which contains hundreds of the separate crystalline scintillation elements. The high Ce:LSO density gives an effective absorption of all gamma quantums emitting from a body of patient examined. A location of the atom of a radioactive isotope in a patient body is determined by means of a time detection of both gammas and numbers of scintillation elements indicated these gamma quantums. In a patient body a part of gamma quantums is scattered because of Compton effect, as a result, the detection of gamma quantums occurs by the crystalline scintillation elements do not arranged in line. Therefore if an scintillation element has a strong afterglow then the indicating system may recognise it as a result of annihilation at a moment, however, actually, this detection is a consequence of exposure to gamma quantum radiation in previous moment of measuring. In the three-dimensional medical tomographs of regular resolution the several thousands $6 \times 6 \times 30$ mm$^3$ scintillation elements are used, they maintain the $6 \times 6 \times 6 = 216$ mm$^3$ volume three-dimensional resolution. Even a strong afterglow of the Ce:LSO crystals does not lead up to the considerable consequences when the comparatively thick $6 \times 6$ mm$^2$ cross-section elements are used for a diagnostics of the cancer illnesses, because a desired recording accuracy may be achieved by an injection of the large doses of radioactive substances or by a reducing of the rate of translation of patient through tomograph's ring.

However condition is changed sharply for MicroPET, which are used for a study of the life processes in vivo, especially, in a human brain or for a measuring of a distribution of medicines in a animal body (mouse, rats) during testing of the new medicines. For MicroPET systems it is necessary to use the devices with a maximal space resolution. The 1×1 mm$^2$ sectioned and even 0.8×0.8 mm$^2$ sectioned scintillation elements are used just now. The 1 mm$^3$ space resolution is achieved. Because of so small thickness of elements the numerous gamma quantums may cross direct the several scintillation elements at different angles. Consequently, to calculate which part of a scintillation radiation is induced by some or other gamma quantum is a complicate technical task. In this case an afterglow becomes a very undesirable effect, because it reduces an accuracy all system.

The afterglow and thermoluminescence phenomena are explored circumstantially for the Ce:LSO crystals (P. Dorenbost, C. van Eijekt, A. Bost, Melcher "Afterglow and thermoluminescence properties of $Lu_2SiO_5$:Ce scintillation crystals", J.Phys.Condens.Matter 6 (1994), pp. 4167–4180). According to this article an afterglow is observed both in the crystals having a high light yield and a low light yield, and a conclusion is that an afterglow is a property immanent to the Ce:LSO substance.

It is known substance the cerium doped gadolinium oxyorthosilicate, $Ce_{2y}Gd_{2(1-x-y)}A_{2x}SiO_5$, where A is at least one element selected from the group La (lanthanum) and Y (yttrium), the x and y values are varied within the limits $0<x<0.5$ and $1\times10^{-3}<y<0.1$ (U.S. Pat. No. 4,647,781, Mar. 3, 1987). The main limitation of this group of scintillation crystals is a low light yield in comparison with the Ce-doped lutetium oxyorthosilicate, $Ce_{2x}Lu_{2(1-x)}SiO_5$, described above.

The known method of crystal growing of the large size Ce-doped lutetium oxyorthosilicate, Ce:LSO, is described in the U.S. Pat. No. 6,413,311, where the Ce:LSO boules up to 60 mm in diameter and 20 cm long are grown by Czochralski technique. An appreciable demerit of these large-sized Ce:LSO boules is that a light yield is strongly differed even within a boule, decreasing to 30%–40% from a top to a bottom of a boule. Furthermore, a scintillation decay time (a time of luminescence) may be varied over the wide range of values from 29 nanoseconds to 46 nanoseconds, at that an energy resolution value may fluctuate within the 12%–20% limit. Such a large spread in performance leads up to necessity during an industrial production to grow a large number of boules by Czochralski method, to cut them into parts (packs), to test each pack and on the basis of such tests to select the packs which possibly to utilize for fabrication of scintillation elements for medical tomographs.

It is known the scintillation crystals, $LU_{2(1-x)}Me_{2x}Si_2O_7$, where LU is lutetium-based alloy which also includes one or more of Sc, Yb, In, La, and Gd; where Me is Ce or cerium partially substituted with one or more of the elements of the lanthanide family excluding lutetium; and where x is defined by the limiting level of LU substitution for Me in a monoclinic crystal of the lutetium pyrosilicate structure (U.S. Pat. No. 6,437,336). The crystal is formed by crystallization from a congruent molten composition of $Lu_{2(1-x)}Me_{2x}Si_2O_7$, a congruent composition allows to use up to 80% of initial melt, and the crystals exhibit reproducible scintillation response to gamma radiation, a light yield spread over volume of boule did not exceed 20% and this commercial parameter was significantly better than for Ce:LSO crystals. However, the $Lu_{2(1-x)}Me_{2x}Si_2O_7$ crystals appreciably conceded to the $Lu_2SiO_5$ crystals in the basic scintillation parameters, namely, the light yield and density. Thus the lutetium oxyorthosilicate crystals, Ce:LSO, are a more preferable scintillator for utilization in a three-dimensional positron-electron tomography, because a tomograph based on these crystals is a more sensitive and, in consequence, a dose of radioactive medicaments, adding in the blood of a patience on early stage of cancers, is reduced.

It is known the lithium containing scintillation substance of the cerium doped yttrium silicate of chemical formula $LiHSiO_4$, (M. E. Globus, B. V. Grinev "Inorganic scintillators", publishing house 'AKTA' Kharkov, (2000) p. 51). The 5%$Ce^{3+}$-doped $LiYSiO_4$ crystal has a peak of luminescence at 410 nm, a luminescence time constant is equaled to 38 ns and a maximal light yield at detection of gamma quantums is 1000 photons/Mev, this value is two and half time less than for the known lutetium oxyorthosilicate scintillating crystals, $Ce_{2x}Lu_{2(1-x)}SiO_5$. A low efficient detection of gamma radiation is resulted from a low density of scintillator is equaled 3.8 g/cm$^3$. This substance may be utilized for detection of neutron radiation, however material is a low efficient for a gamma radiation.

It is known the lithium containing scintillation substance of the cerium doped lutetium silicate of chemical formula $LiLuSiO_4$, (M. E. Globus, B. V. Grinev "Inorganic scintillators", publishing house 'AKTA' Kharkov, (2000) p. 51). The 1%$Ce^{3+}$-doped $LiLuSiO_4$ crystal has a peak of luminescence at 420 nm, a luminescence time constant is equaled to 42 ns and a maximal light yield at detection of gamma radiation is about 30000 photons/Mev, this value is 10% higher than for the known lutetium oxyorthosilicate scintillating crystals, $Ce_{2x}Lu_{2(1-x)}SiO_5$. However, an essential limitation of given crystal is a low density equaled to 5.5 g/cm$^3$. Such small density does not allow to use these crystals in tree-dimensional tomographs (Fully-3D PET camera) and, especially, for MicroPET systems, because the basic requirement for scintillating crystal for these applications is an attenuation length of gamma radiation, which should be less then 1.5 cm (W. M. Moses, S. E. Derenzo "Scintillators for positron emission tomography", Conference SCINT'95, Delft, The Netherlands (1995), LBL-37720). This parameter is equaled 2.67 cm for crystal having a density of 5.5 g/cm$^3$, whereas for the $Ce_{2x}Lu_{2(1-x)}SiO_5$ crystal of 7.4 g/cm$^3$ density an attenuation length is equaled 1.14 cm.

The Ce:LiYSiO$_4$ and Ce:LiLuSiO$_4$ crystals can not be recognised as a prototype for any variants of the given invention, because they are differed both a chemical formula and a crystal structure, which defines a crystal density. A high crystal density is a basic parameter for the applications which are the aim of the given invention.

The chemical formulae of the given invention are the numerous crystals of the solid solutions on the basis of the silicate crystal containing a cerium, Ce, and crystallising in the monoclinic syngony, spatial group B2/b, Z=4, and crystallising in a hexagonal syngony of apatite structural type with a spatial group P6$_3$/m, Z=1.

It is known the mono-cation cerium silicate crystallising in an apatite-brytolite structural type, $Ce_{9.33}\square_{0.67}(SiO_4)_6O_2$, where $\square$ is a cation vacancy (A. M. Korovkin, T. I. Merkulyaeva, L. G. Morozova, I. A. Pechanskaya, M. V. Petrov, I. R. Savinova "Optical and spectral-luminescence properties of the orthosilicate crystals of lanthanide" Optics and Spectroscopy, value 58, issue 6 (1985) p. 1266–1269) and the double silicate of cerium, $LiCe_9(SiO_4)_6O_2$, (I. A. Bondar, N.

V. Vinogradova, L. N. Dem'yanets et al. "Silicates, germanates, phosphates, arsenates, and vanadates. Chemistry of rare elements" monograph M. Nauka, (1983) 288 p.). A cerium presents in the $Ce_{9.33}\square_{0.67}Si_6O_{26}$ and $LiCe_9Si_6O_{26}$ crystals, however, a luminescence is completely quenched in them, this is explained by a concentration quenching in consequence of high concentration of cerium ions in crystals. These crystals are not applicable for utilization as a scintillator. An analogue of the substance claimed in the items 16, 17, 18 of given invention is a crystal of mono-cation cerium silicate, $Ce_{9.33}\square_{0.67}Si_6O_{26}$, since it has the same symmetry, $P6_3/m$, $Z=1$, and has a closest composition to the variants aforecited. An analogue of the substance claimed in the items 19, 20, 21 of given invention is a crystal of double cerium silicate, $LiCe_9Si_6O_{26}$, since it has the same symmetry, $P6_3/m$, $Z=1$, and has a closest composition to the variants aforecited. Both the $Ce_{9.33}\square_{0.67}Si_6O_{26}$ crystal and the $LiCe_9Si_6O_{26}$ crystal cannot be accepted as prototypes for each variant of scintillation substance of given invention since they are not a scintillation material, i.e. these crystals do not have a generic character of given invention reflecting a purpose.

A computer search of chemical compounds in the international X-ray library's database (PDF Database, International Center for Diffraction Data, Newton Square, Pa., U.S.A.) has shown that the individual chemical compounds on a basis mono-cations and doubles silicates, $R_{9.33}\square_{0.67}(SiO_4)_6O_{26}$ and $LiR_9Si_6O_{26}$, respectively, where R=La, Sm, Nd, Gd, Ce are known. However, to our knowledge, there are no patents or publications in which these compounds were additionally doped with cerium what is necessary for an initiation of scintillation properties. Therefore the $R_{9.33}\square_{0.67}(SiO_4)_6O_2$ and $LiR_9Si_6O_{26}$ substances, where R=La, Gd or their mixture, it is necessary to consider as an utilization of known substance on a new purpose.

The nearest analogue chosen as a prototype for all variants of the claimed scintillation substance, is a scintillation substance (variants) patented in the 2157552 patent, Russia, and the U.S. Pat. No. 6,278,832 patent, USA. The chemical formulae of this invention represent the numerous crystals of solid solutions of oxyorthosilicate crystal, including cerium, Ce, and crystallising in the $Lu_2SiO_5$ structural type with space group B2/b, Z=4, which composition is represented by the chemical formula $Ce_xLu_1A_{1-x}SiO_5$, where A is Lu and at least one element selected from the group consisting of Gd, Sc, Y, La, Pr, Nd, Sm, Eu, Tb, Dy, Ho, Er, Tm, and Yb. Other elements of periodic table can be occurred in a crystal as the impurities in the starting oxides or can be introduced into composition during a crystal growth or in a result of annealing in a special atmosphere. Partially the similar results are achieved in the U.S. Pat. No. 6,323,489. This patent protects the lutetium-yttrium oxyorthosilicate crystal of composition having the chemical formula $Ce_zLu_{2-x-z}Y_xSiO_5$, where $0.05<x<1.95$ and $0.001<z<0.02$. The main disadvantage of the above mentioned inventions is the use only molar ratio equaled to $50\%Lu_2O_3/50\%SiO_2=1$ of starting oxides for all patented scintillation materials, that corresponds exactly to stoichiometric composition of $Lu_2SiO_5$ structure. For all mixed crystals simultaneously containing several rare-earth ions, the ratio of 50% of the mix of different elements and 50% of $SiO_2$ has been used. This composition does not allow to grow by Czochralski method the large commercial (diameter more than 80–100 mm) coating lutetium and Ce-doped crystals having a high uniformity of scintillation parameters on all volume of boule. Additionally, the crystals of stoichiometric composition cracked when being sawed for scintillation elements, for example, in the size of 0.8×0.8×10 mm³. Another essential disadvantage of specified scintillation materials is the presence of oxygen vacancies which increase a light output and reduce a probability of cracking of the boules at sawing, however, simultaneously, the presence of oxygen vacancies in two–four times increases an intensity of afterglow (thermoluminescence) after gamma-radiation of scintillation material.

Another confirmation of basic drawback of composition characterised by the $50\%/Lu_2O_3/50\%SiO_2$ molar ratio of oxides is the information described in U.S. Pat. No. 5,660,627. This patent protects a method of growing of lutetium orthosilicate crystal with a plane front of crystallization by Czochralski method from a melt of $Ce_{2x}Lu_{2(1-x)}SiO_5$ chemical formula, where $2\times10^{-4}<x<6\times10^{-2}$. The gamma luminescence spectra of crystals grown with a conical front of crystallization and with a plane front of crystallization have the strong, fundamental differences both in a shape and in a position of maximum of luminescence. So the appreciable differences result from the composition of the initial melt, which has the $50\%Lu_2O_3/50\%SiO_2$ mole ratio of main components. A crystal growing from this melt has a composition differed from the composition of melt, the gradient of concentration is observed along a crystal cross-section, and the real $Ce_{2x}Lu_{2(1-x)}/Si$ ions ratio is differed from the ratio of 2/1=2 formula units. For the confirmation of the main declared in the U.S. Pat. No. 5,660,627 the crystals 26 mm in diameter were grown at the 0.5 mm/hour and 1 mm/hour rates, however, even at these very advantageous growth parameters, the crystals grown with a conical crystallization front can not be used for the commercial applications because of cracking and spread of scintillation performance.

For many years the growing of crystals with a planar crystal-melt interface by Czochralski method is used for commercial production of optical and piezoelectric materials, that is described in detail in the hundreds of papers in scientific journals and books. The well known commercial lithium metaniobate crystal (R. L. Byer, J. F. Young "Growth of High-Quality $LiNbO_3$ Crystals from the Congruent Melt" Journal of Appl. Phys. 41, N6, (1970), p. 2320–2325) is being grown by Czochralski method from a melt of congruent composition, $Li_{0.946}NbO_{2.973}$. having the ratio of initial oxides is equaled to $Li_2O/Nb_2O_5=0.946$, the congruent composition is differed from an ordinary, stoichiometric composition of lithium metaniobate, $LiNbO_3$, where a ratio of component is equaled to $50\%LiO/50\%Nb_2O_5=1$. (P. Lerner, C. Legras, J. Dumas "Stoichiometrie des mohocristaux de metaniobate de lithium", Journal of Crystal Growth, 3,4 (1968) p. 231–235). An existence of non-stoichiometric compounds is directly concerned with a structure of real crystal, in which the vacant lattice sites exist, and the excess atoms of one of the elements are placed in the crystal interstitial sites. (P. V. Geld, F. A. Sidorenko "Dependence of physical-chemical properties of non-stoichiometric compounds on structure of short-range order" Izvestia AN SSSR, seria Inorganic materials, 1979, v. 15, #6, p. 1042–1048). As a result, a ratio of components forming a structure does not correspond to the whole-numbered indices, and the chemical formulae of such compounds are described by the fractional numbers. A chemical composition is named the congruent composition, if a composition of melt is coincided with a composition of crystal growing from this melt. All the physical and mechanical properties of crystals grown from the melts of congruent compositions maintain the values constant over all volume of boule. For some applications a near stoichiometric composition, $Li_2O/Nb_2O_5=1$, is a preferable use, U.S. Pat. No. 6,464,777 B2 dated Oct. 15, 2002. This patent clearly illustrates as the small variations of crystal composition lead up to the appreciable alterations of physical properties of crystal and this is important for the practical applications.

It is known (in the book D. T. J. Hurle "Crystal Pulling from the Melt" Springer-Verlag, Berlin, Heidelberg, New-York, London, Paris, Tokyo, Hong Kong, Budapest, 1993, p. 21) that because of the complex oxide systems of optics and electronics interests, such as garnets and spinels, do not correspond to a congruently melting composition it is necessary to induce growth only at a very low rate in order to give time for diffusion away from the interface of the excess component. Failure to do this leads to dramatic degradation in the perfection of the crystals due to the occurrence of constitutional supercooling. A search of congruent composition or very near to congruent composition is an important stage of development of commercial production of all optical materials, however, the authors of given invention do not know the data about congruent composition (or near to congruent composition) of lutetium oxyorthosilicate published in the scientific journals or in the patents. All known publications are dedicated to the crystals, in which a ratio of formula units, $(Ce_{2x}+Lu_{2(1-x)})/Si$, is exactly equaled to 2/1.

Generalising the above-mentioned, we may conclude that a basic technical drawback, immanent to both the known scintillation crystals on the basis of lutetium orthosilicate, $Ce_xLu_{2x}SiO_5$, and prototype's crystals and a method of making of these crystals, are a longitudinal heterogeneity of optical quality of grown crystals, a heterogeneity of the basic scintillation parameters both in a bulk of boule grown by Czochralski method and heterogeneity from boule to boule grown in alike conditions and, at last, a low growth rate. These drawbacks substantially arise from the use in Czochralski method of melt having a composition which characterised a ratio of formula units, (Ce+Lu)/Si, which is exactly equaled to 2/1, i.e. the reason of these drawbacks resides in a non-congruent composition of melt. At the existence of congruent point, a crystal growth from a stoichiometric composition leads up to that the segregation coefficients of both the host crystal components, Lu, Si, and the additional component, Ce, are differed from unit, and, moreover, a crystal composition is shifting from the congruent point as a crystal pulling, that results in dramatic degradation of crystal quality despite on the extremely low growth speed. A segregation coefficient of component is a ratio of component's quantity in a crystal to component's quantity in a melt. Another common technical demerit of scintillation crystals on the base of lutetium orhtosilicate is the large losses of crystalline material because of cracking during slicing of a large, up to 60 mm in diameter, boules into 1 mm thickness pieces, which in their turn are cut into rods to produce the $1\times1\times10$ mm$^3$ dimensions elements in the quantity of several tens of thousands pieces needed for assembling of one tomograph.

BRIEF SUMMARY OF THE INVENTION

A task of the given invention is a creation of a new scintillation material and a method of its making. The given invention is directed on the solution of task of mass production of the large crystalline boules of scintillation materials grown by directional crystallization method. Scintillation materials should have a large density; a high light yield and a homogeneity of scintillation properties at mass production; reducing of manufacturing cost of finished scintillation elements due to small losses of crystalline substance at mechanical treatment; decreasing of time and afterglow intensity of elements having an optimal chemical composition of crystals. Stepanov's method allows to produce the scintillation substances in the form of crystalline rods of specified size including the elements having a square of cross-section and, therefore, to exclude an expansive slicing of massive crystal. A method of production of scintillation translucent or transparent ceramics in the form of rectangular rods and plates allows also to eliminate expansive losses of scintillation substance during cutting of crystalline boule. Thus, the given invention presents the group of inventions and provides an attainment of several technical results on the basis of different variants of scintillation substances of both crystals and the ceramics, having a high density and representing the rare-earth silicates of different chemical formulae.

The technical task solved by offered group of inventions is a production of large crystalline boules, having a high light output of a luminescence over all volume, grown by directional crystallization method, in particular, the Kyropoulas and Czochralski methods, and also the task of the invention is a reproducibility of scintillation properties of monocrystals grown at mass production.

The first technical task in the specific forms is a composition of scintillation substance having an intensity and an afterglow time less than the known lutetium oxyorthosilicate crystals have, and a light output of proposed substance is comparable or higher than a lutetium oxyorthosilicate has.

The second technical task in the specific forms is a small percent of losses of valuable scintillation elements because of cracking during sawing and manufacturing of scintillation elements for the three-dimensional positron-emitting tomographs. In particular, for the high space-resolved medicine devices, for example, for recording positron-emitting isotopes placed in the alive biological objects (micro-tomographs—MicroPET), the elements of $1\times1\times20$ mm$^3$ or $0.8\times0.8\times10$ mm$^3$ dimensions are required.

The third technical task in the specific forms is the method of growing of scintillation monocrystals by directional crystallization method. The term <<a directional crystallization>> denotes any method of single crystal growth method, including Czochralski method, Kyropoulas method, Bridgman method and others known methods.

The solutions of said tasks are achieved due to the use of scintillation substances both crystal and ceramics having the compositions on the basis of ten variants of substances unified by the common structural types, the chemical formulae and the method of fabrication of these materials.

Variant #1. The known scintillation substance based on a silicate comprising a lutetium (Lu) and cerium (Ce), in the first variant of given invention a new is a composition of substance is represented by the chemical formula $$Ce_xLu_{2+2y-x}Si_{1-y}O_{5+y},$$

x is a value between $1\times10^{-4}$ f.u. and 0.02 f.u., y is a value between 0.024 f.u. and 0.09 f.u.

The technical result—the creation of scintillation substance having a large density; a high light yield and a homogeneity of scintillation properties during mass production is achieved due to the use of the substance based on a silicate having the congruent composition of basic components.

A technical result in the specific forms of implementation is achieved by way of using a scintillation substance, characterised in that the composition of the substance in the form of a single crystal is represented by the chemical formula $$Ce_xLu_{2.076-x}Si_{0.962}O_{5.038},$$

x is a value between $1\times10^{-4}$ f.u. and 0.02 f.u.

Another technical result, namely mass production of large crystalline boules, having a high light output of a luminescence over all boule volume, a reproducibility of scintillation properties of monocrystals, is achieved by method of making of scintillating material. A single crystal is being grown by a directional crystallization method from a melt made from the charge of the composition defined by the 51.9% $(Lu_2O_3+Ce_2O_3)/48.1\%$ $SiO_2$ oxides mole ratio.

The particular specific forms of invention implementation the technical result, expressed in a de-creasing of production cost of scintillation elements and a reproducibility of physical properties of the samples from boule to boule at mass production, is achieved by way of a growing of single crystal of Czochralski method and a growing of crystal by Kyropoulas method. A new in the given method is the single crystal being grown by Czochralski method and also Kyropoulas method from a melt made from the charge of the composition defined by the 51.9% $(Lu_2O_3+Ce_2O_3)/48.1\%$ $SiO_2$=1.079 oxides mole ratio, this is, so named, a congruence composition. In that oxides ratio the composition of grown crystal is equaled to composition of a melt, this circumstance allows to grow the crystals of more homogeneous in composition and in physical characteristics, than the crystals grown from a melt of stoichiometric composition, 50% $(Lu_2O_3+Ce_2O_3)/50\%$ $SiO_2$=1. A growth of crystals from a melt of congruent composition allows to use more than 80% of melt, this appreciably cheapens a cost of scintillation elements.

Variant #2. The known scintillation substance based on a silicate comprising a lutetium (Lu) and cerium (Ce), in the second variant of given invention a new is a composition of substance is represented by the chemical formula $$Ce_xLu_{2+2y-x-z}A_zSi_{1-y}O_{5+y},$$

where A is at least one element selected from the group consisting of Gd, Sc, Y, La, Eu, Tb, and Ca,
  x is a value between $1\times10^{-4}$ f.u. and 0.02 f.u.,
  y is a value between 0.024 f.u. and 0.09 f.u.,
  z is a value between $1\times10^{-4}$ f.u. and 0.05 f.u.

The technical result—the creation of scintillation substance having a comparatively low cost, a high light yield and a homogeneity of scintillation properties, is achieved due to the use of the substance based on a silicate having the congruent composition of total basic components, (Lu+A+Ce) and Si. The substitution of heavy expensive lutetium for at least one comparatively light element selected from the Gd, Sc, Y, La, Eu, Tb, and Ca group reduces a manufactory cost, reduces a crystal cracking during an after growth annealing and a cutting, increases a light yield, but may cause an inconsiderable decreasing the density. The cheap scintillation crystals having a smaller density of 7.2–7.4 g/cm³, and atomic number of Z=58–63, but a high light yield are useful for numerous applications, for example, in nuclear industry.

A technical result in the specific forms of implementation is achieved by way of using a scintillation substance, characterised in that the composition of the substance in the form of a single crystal is represented by the chemical formula $$Ce_xLu_{2.076-x-z}A_zSi_{0.962}O_{5.038},$$

where A is at least one element selected from the group consisting of Gd, Sc, Y, La, Eu, Tb, and Ca,
  x is a value between $1\times10^{-4}$ f.u. and 0.02 f.u.,
  z is a value between $1\times10^{-4}$ f.u. and 0.05 f.u.

In the specific forms of implementation the detailed technical result, expressed in an increasing of a light yield following by an insignificant decrease of density is achieved by the growing of a scintillation substance, characterised in that the composition of the substance in the form of a single is represented by the chemical formula $$Ce_xLu_{2.076-x-m-n}La_mY_nSi_{0.962}O_{5.038},$$

x is a value between $1\times10^{-4}$ f.u. and 0.02 f.u.,
  m is a value does not exceeding 0.05 f.u.,
  n is a value between $1\times10^{-4}$ f.u. and 2.0 f.u.

Another technical result—mass production of large crystalline boules, having a high light output of a luminescence over all boule volume, a reproducibility of scintillation properties of monocrystals grown during mass production, is achieved by way of growing of scintillating single crystal by a directional crystallization method from a melt made from the charge of the composition defined by mole ratio of oxides 51.9% $(Lu_2O_3+A_2O_3+Ce_2O_3)/48.1\%$ $SiO_2$, where A is at least one element selected from the group consisting of Gd, Sc, Y, La, Eu, and Tb.

The particular specific forms of invention implementation the technical result, expressed in a decreasing of production cost of scintillation elements, reducing a crystal cracking during an after growth annealing and a cutting, and a reproducibility of physical properties of the samples from boule to boule at mass production, is achieved by way of a growing of single crystal of Czochralski method and a growing of crystal by Kyropoulas method. A new in the given method is the single crystal being grown by Czochralski method and also by Kiropoulas method from a melt made from the charge of the composition defined by mole ratio of oxides 51.9% $(Lu_2O_3+A_2O_3+Ce_2O_3)/48.1\%$ $SiO_2$, where A is at least one element selected from the group consisting of Gd, Sc, Y, Ta, Eu, Tb, and Ca.

Variant #3. The known scintillation substance based on a silicate comprising a lutetium (Lu) and cerium (Ce), in the third variant of given invention a new is a substance containing a lithium, Li, in the quantity does not exceeding 0.25 f.u., and the composition of substance is represented by the chemical formula $$Ce_xLi_{q+p}Lu_{2-p+2y-x}Si_{1-y}O_{5+y-p}$$

x is a value between $1\times10^{-4}$ f.u. and 0.02 f.u.,
  y is a value between 0.024 f.u. and 0.09 f.u.,
  q is a value between $1\times10^{-4}$ f.u. and 0.02 f.u.,
  p is a value between $1\times10^{-4}$ f.u. and 0.05 f.u.

The technical result—the creation of scintillation substance having a high light yield, a large density, a homogeneity and reproducibility of scintillation properties during mass production is achieved due to the use of substance based on a silicate containing lithium and having the congruent composition of the basic components.

A technical result in the specific forms of implementation, expressed in a decreasing of production cost of scintillation elements and a reproducibility of physical properties of the samples from boule to boule at mass production, is achieved due to the use of the scintillation substance is characterised in that the composition of the substance in the form of a single crystal containing a lithium Li in the quantity does not exceeding 0.25 f.u. is represented by the chemical formula $$Ce_xLi_{q+p}Lu_{2.076-p-x}Si_{0.962}O_{5.038-p},$$

x is a value between $1\times10^{-4}$ f.u. and 0.02 f.u.,
q is a value between $1\times10^{-4}$ f.u. and 0.2 f.u.,
p is a value between $1\times10^{-4}$ f.u. and 0.05 f.u.

Another technical result—mass production of large crystalline boules, having a high light output of a luminescence over all boule volume, a reproducibility of scintillation properties of monocrystals grown during mass production, is achieved by way of growing of scintillating single crystal grown by a directional crystallization method from a melt made from the charge of the composition defined by mole ratio of oxides 51.9% $(Lu_2O_3+Li_2O+Ce_2O_3)$/48.1% $SiO_2$.

Variant #4. The known scintillation substance based on a silicate comprising a lutetium (Lu) and cerium (Ce), in the fourth variant of given invention a new is a substance containing a lithium, Li, in the quantity does not exceeding 0.25 f.u., and its composition is represented by the chemical formula $$Ce_xLi_{q+p}Lu_{2-p+2y-x-z}A_zSi_{1-y}O_{5+y-p},$$

where A is at least one element selected from the group consisting of Gd, Sc, Y, La, Eu, and Tb.
x is a value between $1\times10^{-4}$ f.u. and 0.02 f.u.,
y is a value between 0.024 f.u. and 0.09 f.u.,
z is a value between $1\times10^{-4}$ f.u. and 0.05 f.u.,
q is a value between $1\times10^{-4}$ f.u. and 0.2 f.u.,
p is a value between $1\times10^{-4}$ f.u. and 0.05 f.u.

The technical result—the creation of scintillation substance having a comparatively low cost, reducing a crystal cracking during an after growth annealing and a cutting, a high light yield and a homogeneity of scintillation properties, is achieved due to the use of the substance based on a silicate having the congruent composition of the total basic components, (Lu+Li+A+Ce) and Si. The substitution of heavy expensive lutetium for at least one comparatively light element selected from the Gd, Sc, Y, La, Eu, and Tb group reduces a manufactory cost, increases a light yield, but may cause an inconsiderable decreasing of density. The cheap scintillation crystals having a smaller density of 7.2–7.4 g/cm$^3$, and atomic number of Z=58–63, but a high light yield are useful for numerous applications, for example, in nuclear industry.

A technical result in the specific forms of implementation is achieved by way of using a scintillation substance, characterised in that the composition of the substance in the form of a single crystal containing a lithium Li in the quantity does not exceeding 0.25 f.u. is represented by the chemical formula $$Ce_xLi_{q+p}Lu_{2.076-p-x-z}A_zSi_{0.962}O_{5.038-p},$$

where A is at least one element selected from the group consisting of Gd, Sc, Y, La, Eu, and Tb,
x is a value between $1\times10^{-4}$ f.u. and 0.02 f.u.,
z is a value between $1\times10^{-4}$ f.u. and 0.05 f.u.,
q is a value between $1\times10^{-4}$ f.u. and 0.2 f.u.,
p is a value between $1\times10^{-4}$ f.u. and 0.05 f.u.

Another technical result—mass production of large crystalline boules, having a low cost, a high light output of a luminescence over all boule volume, a reproducibility of scintillation properties of monocrystals grown during mass production, is achieved by way of growing a single crystal by a directional crystallization method from a melt made from the charge of the composition defined by mole ratio of oxides 51.9% $(Lu_2O_3+Li_2O+A_2O_3+Ce_2O_3)$/48.1% $SiO_2$.

Variant #5. The known scintillation substance based on a silicate comprising a lutetium (Lu) and cerium (Ce), in the fifth variant of given invention a new is a composition of substance represented by the chemical formula $$Ce_xLu_{9.33-x}\square_{0.67}Si_6O_{26}$$

x is a value between $1\times10^{-4}$ f.u. and 0.1 f.u.

The technical result—the creation of scintillation substance having a large density; a high light yield is achieved due to the making of the mono-cation silicate crystallized in a hexagonal syngony of apatite spatial group $P6_3/m$, Z=1, as well as the expense of an advantageous content of $Ce^{3+}$ ions in the substance.

Variant #6. The known scintillation substance based on a silicate comprising a lutetium (Lu) and cerium (Ce), in the sixth variant of given invention a new is a substance containing a lithium, Li, and the composition of substance is represented by the chemical formula $$Ce_xLi_{q+p}Lu_{9.33-x-p}\square_{0.67}Si_6O_{26-p},$$

x is a value between $1\times10^{-4}$ f.u. and 0.1 f.u.,
q is a value between $1\times10^{-4}$ f.u. and 0.3 f.u.,
p is a value between $1\times10^{-4}$ f.u. and 0.25 f.u.

The technical result—the creation of scintillation substance having a large density; a high light yield is achieved due to the making of the mono-cation silicate crystallized in a hexagonal syngony of apatite spatial group $P6_3/m$, Z=1, as well as the expense of an advantageous content of $Ce^{3+}$ ions in the substance.

Variant #7. The known scintillation substance based on a silicate comprising a lutetium (Lu) and cerium (Ce), in the seventh variant of given invention a new is a substance containing a lithium, Li, and the composition of substance is represented by the chemical formula $$Ce_xLi_{q+p}Lu_{9.33-x-p-z}\square_{0.67}A_zSi_6O_{26-p},$$

where A is at least one element selected from the group consisting of Gd, Sc, Y, La, Eu, and Tb,
x is a value between $1\times10^{-4}$ f.u. and 0.1 f.u.,
q is a value between $1\times10^{-4}$ f.u. and 0.3 f.u.,
p is a value between $1\times10^{-4}$ f.u. and 0.25 f.u.,
z is a value between $5\times10^{-4}$ f.u. and 8.9 f.u.

The technical result—the creation of scintillation substance having a large density, reducing a crystal cracking during an after growth annealing and a cutting, a high light yield is achieved due to the making of the mono-cation silicate crystallized in a hexagonal syngony of apatite spatial group $P6_3/m$, Z=1, as well as the expense of an advantageous content of $Ce^{3+}$ ions in the substance.

Variant #8. The known scintillation substance based on a silicate comprising a lutetium (Lu) and cerium (Ce), in the eighth variant of given invention a new is a substance containing a lithium, Li, in the quantity one formula units and the composition of substance is represented by the chemical formula $$Ce_xLiLu_{9-x}Si_6O_{26},$$

x is a value between $1\times10^{-4}$ f.u. and 0.1 f.u.

The technical result—the creation of scintillation substance having a large density; a high light yield is achieved due to the making of the double silicate crystallized in a hexagonal syngony of apatite spatial group $P6_3/m$, Z=1, as well as the expense of an advantageous content of $Ce^{3+}$ ions in the substance.

Variant #9. The known scintillation substance based on a silicate comprising a lutetium (Lu) and cerium (Ce), in the ninth variant of given invention a new is a substance containing a lithium, Li, in the quantity exceeding 1.0 f.u. and the composition of substance is represented by the chemical formula

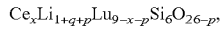
$$Ce_xLi_{1+q+p}Lu_{9-x-p}Si_6O_{26-p},$$

x is a value between $1\times10^{-4}$ f.u. and 0.1 f.u.,
q is a value between $1\times10^{-4}$ f.u. and 0.3 f.u.,
p is a value between $1\times10^{-4}$ f.u. and 0.25 f.u.

The technical result—the creation of scintillation substance having a large density; a high light yield is achieved due to the making of the double silicate crystallized in a hexagonal syngony of apatite spatial group P6$_3$/m, Z=1, as well as the expense of an advantageous content of Ce$^{3+}$ ions in the substance.

Variant #10. The known scintillation substance based on a silicate comprising a lutetium (Lu) and cerium (Ce), in the tenth variant of given invention a new is a substance containing a lithium, Li, in the quantity exceeding 1.0 f.u. and the composition of substance is represented by the chemical formula $$Ce_xLi_{1+q+p}Lu_{9-x-p-z}A_zSi_6O_{26-p},$$

where A is at least one element selected from the group consisting of Gd, Sc, Y, La, Eu, and Tb,
x is a value between $1\times10^{-4}$ f.u. and 0.1 f.u.,
q is a value between $1\times10^{-4}$ f.u. and 0.3 f.u.,
p is a value between $1\times10^{-4}$ f.u. and 0.25 f.u.,
z is a value between $5\times10^{-4}$ f.u. and 8.9 f.u.

The technical result—the creation of scintillation substance having a large density, reducing a crystal cracking during an after growth annealing and a cutting, a high light yield is achieved due to the making of the double silicate crystallized in a hexagonal syngony of apatite spatial group P6$_3$/m, Z=1, as well as the expense of an advantageous content of Ce$^{3+}$ ions in the substance.

For all enumerated variants the presence of cerium ions, Ce$^{3+}$, is a mandatory requirement, because a scintillation under gamma and X-ray radiation combines with luminescence originating from the Ce$^{3+}$ ion 5d→$^2$F$_{5/2}$ transfer. For all variants of substances the maximum of Ce$^{3+}$ ion luminescence is in the blue 410–450 nm region of spectrum. This band is an optimal for detection of radiation with both the photomultiplier tubes and semiconductor radiation detectors. For measurements in that region the ordinary, commercial photomultiplier tubes having inexpensive glass input window are used, this reduces the cost of medical devices in comparison with devices in which the scintillation crystals, having an emission peak in ultraviolet region of spectrum, are utilized. A high quantum yield of cerium ions luminescence is also the representative indication of all crystals having the above-mentioned chemical formulas. The 5%–9% quantum yield characterizes which part of gamma-quantum energy is converted into Ce$^{3+}$ ions emission, and which part of energy (91%–95%)) is dissipated at thermal oscillations of lattice atoms. An essential scintillation parameter, a light yield depends directly on concentration of cerium, Ce$^{3+}$, ions in a substance/crystal.

For all variants the lower limit for the cerium ions is determined by the fact that at the content of Ce$^{3+}$ in the quantity of less than $1\times10^{-4}$ f. units, the effectiveness of a scintillation luminescence of Ce$^{3+}$ becomes insignificant because of the small concentration. With the concentration of cerium lower than the above limit, the implementation of the technical task cannot be reached, namely it is not possible to achieve a light yield sufficient for practical utilization.

For practical applications the crystals having the higher cerium ions concentration are required because such crystals have appreciably higher light yield. However, the very high cerium concentration leads to the several negative results. Firstly, the crystals with a high cerium concentration have a bad optical quality, the scattering centers are presented in crystals. Secondly, a reducing of light yield is taken place because of both a lowering of optical quality and a decreasing of quantum efficiency, which happens due to an interaction of neighbour cerium ions, so named, an effect of concentration quenching of luminescence. Therefore the upper limit for cerium ions is set 0.02 f. units for all substances of given invention, which are crystallized in a monoclinic syngony, at the structural type Ce$_x$Ln$_{2-x}$SiO$_5$ with a spatial group B2/b, Z=4. The upper limit of 0.1 f. units is set for the Ce$_x$Ln$_{9.33-x}$□$_{0.67}$SiO$_{26}$ and Ce$_x$LiLn$_{9-x}$SiO$_{26}$ substances being crystallized in a hexagonal syngony, an apatite structural type with a spatial group P6$_3$/m, Z=1. These limits are defined by experimentally. When the concentration is above indicated limits, then the formation of numerous scattering centers of light takes place during crystallization and, therefore, the implementation of such defective crystals in medical and technical devices is not possible.

The technical result, namely a production of large crystalline boules, having a high light output of a luminescence over all volume, a reproducibility of scintillation properties of monocrystals grown at mass production, a small percent of losses of valuable scintillation elements because of cracking during sawing and manufacturing of scintillation elements, is achieved due to the growing of scintillation crystals of congruency composition. The common improvement sign for the variants #1, #2, #3 and #4 is a value of ratio of rare-earth ions and silicon ions in chemical composition of substance, i.e. a composition characterized by a ratio of formula units of (Lu$_{2-x+2y}$+Ce$_x$)/Si$_{1-y}$ and (Lu$_{2-x+2y-z}$+Ce$_x$+A$_z$)/Si$_{1-y}$ is differed from a 2/1 ratio which is obligatory 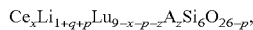 exactly equaled to 2 for all known scintillation substances on the basis of orthosilicates. For the substances of given invention the ratios of formula units of (Lu$_{2-x+2n}$+Ce$_x$)/Si$_{1-y}$ and (Lu$_{2-x+2y-z}$+Ce$_x$+A$_z$)/Si$_{1-y}$ are varied within the limit from 2.077 to 2.396 that corresponds to the mole oxides ratio equaled to 51.2%(Lu$_2$O$_3$+Ce$_2$O$_3$+A$_2$O$_3$)/48.8%SiO$_2$=1.049 and 54.5%(Lu$_2$O$_3$+Ce$_2$O$_3$+A$_2$O$_3$)/45.5%SiO$_2$=1.198, respectively. These magnitudes correspond to the compositions of substances Ce$_x$Lu$_{2+2y-x}$Si$_{1-y}$O$_{5+y}$, Ce$_x$Lu$_{2+2y-x-z}$A$_z$Si$_{1-y}$O$_{5+y}$, Ce$_x$Li$_{q+p}$Lu$_{2+2y-x-z-p}$A$_z$Si$_{1-y}$O$_{5+y-p}$, where variable y is changed within the limits from 0.024 f. units to 0.09 f. units. We have measured specified magnitude using the commercial device for the electronic microanalysis (Cameca Camebax SX-50, operating at 20 kV, 50 mA and diameter of the beam of 10 microns), an accuracy of measurements of composition was ±0.003 f. units, in mole percents an accuracy was ±0.15 mol %. The mechanically polished samples for measurements were cut from the crystals grown by directional crystallization method from the melts having the mole ratios of components (Lu$_{2-x}$+Ce$_x$)/Si and (Lu$_{2-x-y}$+Ce$_x$+A$_z$)/Si within the limits from 1.77 to 2.44. On the basis of X-ray phase analysis and measurements of melting point of series of powdered compositions, the authors of the given invention have defined the part of phase diagram for region of existence of lutetium oxyorthosilicate in the Lu$_2$O$_3$—SiO$_2$ system (FIG. 1). The process of changing of composition of solid solutions of lutetium oxyorthosilicate crystals (phase "S") in depending on a composition of melt is exhibited on FIG. 1. In accordance with the traditional notations, a liquid phase is symbolized by "L" on this diagram. The maximum of melting point temperature of solid solutions "S" corresponds to the composition of 51.9 mol %$Lu_2O_3$+48.1 mol %$SiO_2$ on constitution diagram. The region of existence of phase "S" is surrounding by the fields of two-phase equilibrium L+S, $Lu_2O_3$+S and S+$Lu_2Si_2O_7$.

The phase diagram (FIG. 1) was detailed for the near equilibrium conditions of solidification during crystal growing from the melts having the different chemical compositions. The comparison of composition of initial melt with the composition of crystal grown from that melt determines that a solidification occurs in accordance with a liquidus and a solidus lines shown on FIG. 1. The compositions of melts have been set at weighing of the initial chemicals, the temperatures of melts also were taking in account during experiments. The crystals growing were carried out at the conditions of low gradients of temperature and with the crystals pulling rates near 0.3 mm/hour, that maintained an attaining of the effective segregation coefficients of the $Lu^{3+}$ and $Si^{4+}$ ions between a melt and a growing crystal at the conditions near to equilibrium.

The liquidus and solidus lines on FIG. 1 show, that the lutetium oxyorthosilicate crystals may have the compositions characterized by the different ratio of initial $Lu_2O_3$ and $SiO_2$ oxides, namely, a content of chemicals is within the range the 44.5–50.5 mol % for $SiO_2$ and the 55.5–49.5 mol % for $Lu_2O_3$. However, for the practical purposes the specified range of compositions is interested only partially, three compositions of melt denoted by the arrows numbered 1, 2, and 3 illustrate this. The arrow 1 denotes the 50% $Lu_2O_3$+50% $SiO_2$ composition of initial melt. It should be pointed out that the composition of crystal growing from this melt has the ratio of basic components less than 50.9 mol % $Lu_2O_3$/49.1 mol % $SiO_2$=1.037. To grow the crystal of composition having the ratio of basic components equaled exactly to 50 mol % $Lu_2O_3$/50 mol % $SiO_2$=1, it is required to use a melt of composition denoted by arrow 2, i.e. the ratio of basic components in the melt is approximately equaled to 46 mol % $Lu_2O_3$+54 mol % $SiO_2$=0.852.

An optimal composition of oxides mixture (a charge) for the growth of scintillation crystal of high quality in the conditions of the low temperature gradients (a large diameter of crucible) is the composition denoted by arrow 3. In this case the segregation coefficients of basic components are equaled to a unity, and a composition of charge of melt coincides with the composition of growing crystal, both composition of charge and composition of grown crystal have the contents of basic components characterized by the mole ratio of 51.9% $Lu_2O_3$+48.1% $SiO_2$=1.079.

Therefore, FIG. 1 shows the unique solution of technical task in the specific forms of implementations of first, second, third, and fourth variants describing the scintillation substances for the growing of oversize single crystals by Kyropoulos method, and also for the growing of big single crystals by Czochralski method utilizing the optimal composition of initial oxides having the mole ratio of 51.9% ($Lu_2O_3$+$Ce_2O_3$)/48.1% $SiO_2$, and the compositions of charge of melt and grown crystals coincide and are described by the chemical formula $Ce_xLu_{2.076-x}Si_{0.962}O_{5.038}$

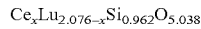

where x is a value between $1\times10^{-4}$ f.u.

The evidence of choice of the lower and upper values of the ratios range of the initial $Lu_2O_3$ and $SiO_2$ oxides for the substances of variants #1, #2, #3 and #4 is illustrated on FIG. 1. The lower limit of a components content in a crystal relative to a lutetium is determined by the oxides mole ratio of 51.2% ($Lu_2O_3$+$Ce_2O_3$)/48.8% $SiO_2$=1.049, which corresponds to the value of variable y=0.024 in a chemical formula of scintillation substance. The lower boundary is determined by an accuracy of the chemical and physical experimental methods of measurements of lutetium and silicon in a crystal. Such accuracy allows in a unique manner to distinguish the substances/crystals chemical compositions of the given invention from the compositions of known lutetium orthosilicate scintillation crystals having the 50% ($Lu_2O_3$+$Ce_2O_3$)/50% $SiO_2$ mole ratio of components.

The upper boundary of a components content in a crystal relative to a lutetium is determined by the oxides mole ratio of 54.5% ($Lu_2O_2$+$Ce_2O_3$)/45.5%$SiO_2$=1.198, which corresponds to the value of variable y=0.09 in a chemical formula of scintillation substance. This boundary is determined experimentally. In a case of further increasing of a $Lu_2O_3$ content in an initial melt and, consequently, in a crystal the scattering centers are occurred, that decreases a light yield, and, as a result, a technical result of given invention cannot be reached. After conversion of the values of compositions of the lower and upper boundaries into formula units for the #1, #2, #3 and #4 variants, the range of compositions in formula units defined by the ratios of ($Lu_{2-x}$+$Ce_x$)/Si and ($Lu_{2-x-y}$+$Ce_x$+$A_z$)/Si is lying within the limit from 2.077 to 2.396. These values correspond to the compositions described by the chemical formulae $Ce_xLu_{2+2y-x}Si_{1-y}O_{5+y}$, $Ce_xLu_{2+2y-x-z}A_zSi_{1-y}O_{5+y}$, and $Li_qCe_xLu_{2+2y-x-z}A_zSi_{1-y}O_{5+y}$, where y varies between the limits from 0.024 f. unites to 0.09 f. units.

Should make a point of the compositions of lutetium oxyorthosilicate solid solutions crystals, i.e. the compositions, which are to the right side from the maximum of their maximal melting point, FIG. 1. This is a region of the crystal compositions lying to the right side bounded by a maximal $SiO_2$ solubility, corresponds to a solid solution composition having a molar ratio of 49.5% $Lu_2O_3$/50.5% $SiO_2$=0.980, and a left boundary of crystal composition having the value of 50.9% $Lu_2O_3$/49.1% $SiO_2$=1.037, is determined by the 50% $Lu_2O_3$+50% $SiO_2$ composition of melt, FIG. 1.

Let us determine the crystals of which compositions may grow by a directional crystallization method from a melt obtained from a charge of the stoichiometric composition, 50% $Lu_2O_3$/50% $SiO_2$=1.000, denoted by the arrow 1 on FIG. 1. Depending on the technology peculiarities, namely the thermal conditions of a growing, the temperature gradients on a melt-crystal interface determining by a crystal diameter, the components segregation coefficients may vary from 1 to the equilibrium values which in its turn are determined in accordance with the constitution diagram FIG. 1. As a result, from a charge of the stoichiometric composition of 50% $Lu_2O_3$+50% $SiO_2$ may grow the crystals of compositions being in the range bounded by the lower limit of a component ratio of more than 49.5% $Lu_2O_3$/50.5% $SiO_2$=0.980, and the upper limit of a component ratio of less, than 50.9% $Lu_2O_3$/49.1% $SiO_2$=1.037. In formula units this corresponds to the values range in which the variable y is more than (−0.01) ±0.003 f. units, but less than 0.018 ±0.003 f. units. The given range of the crystal compositions has not been patented in the known patents. However the given range cannot be a subject of new invention because the crystals having a composition in the given range are covered by a concept of existing state of the arts. These crystals do not maintain an improvement of technical performance in comparison with the known substances. A growing of a lutetium oxyorthosilicate crystal of high quality requires to use the congruent composition of melt, which appreciably differs from the composition of crystal growing from this melt. The crystals grown from a melt of stoichiometric composition have an appreciable variation of chemical composition along a length, and also an extremely large variation of all physical and scintillation parameters both along the length and diameter because the segregation coefficients of silicon and lutetium are differed from 1. Such crystals are utilized for the scientific researches, however a commercial production of crystals having a similar composition are of no interest because the percent of a chemical oxides-to-scintillation element yield is a low, a manufacturing cost is an extremely high.

In the specific forms of implementation the scintillation substances claimed in variants from the first to the fourth inclusive are achieved in the forms both a polycrystal/ceramics and a single crystal.

The manner of ceramics making by the method of hot-pressing, for example, the $Gd_2O(SiO_4)$:Ce scintillation ceramics is described, for example, in the paper (W. Rossner, R. Breu "Luminescence properties cerium-doped gadolinium oxyorthosilicate ceramics scintillators" Proc.Int. Conf. on Inorganic Scintillators and Their Application, STINT'95, Netherlands, Delft University, 1996, p. 376–379). In another manner of fabrication of high optical quality ceramics-scintillator the water solutions of Lu—Ce—A chlorides, where A is at least one of the elements of group Gd, Sc, Y, La, Eu, and Tb, and the $SiCl_4$ liquid are used as the initial materials for a charge preparation. Into the mixture of said components a water solution of ammonium hydrocarbonate is added. Then the solution is being washed, filtered, and dried. The calcined at 1400° C. mixture of oxides is being stirred with a dissolvent and the fusible dopants, promoting a diffusion of atoms along grain boundaries on a stage of final high-temperature annealing. As the admixtures the numerous compounds not affecting a luminescence of cerium $Ce^{3+}$ ions can be used. After removing of organic components and trace of water the modified mixture is pressed in hydrostatic press at 2000 atmospheres. Then, during several hours, the pressed ceramics bars (rectangular or another form) are annealed in vacuum at temperatures 70°–150° C. lower the melting point of given ceramic composition. To remove the color centers and to improve an optical quality, the sintered bars is annealed in an oxygen containing atmosphere at final stage of processing. Such way a translucent ceramics-scintillator and a high optical quality ceramics are produced. A ceramics scintillation substance has a row of advantages in comparison with the single crystals, namely: an appreciable cheaper technology of scintillators production; ingot-to-scintillation element high product yield (no cracks); a saving up to 20%–50% of scintillation substance because of elimination of cutting from technology of fabrication of fine-face scintillation elements; a uniform distribution of cerium Ce ions in a polycrystalline body; a shortening of scintillation elements processing time; any desirable shaping of scintillation elements.

In the specific forms of implementation a method of directional crystallization is used to make a scintillation substance in the form of single crystal. A new in a proposed method is that a single crystals are being grown by a directional crystallization method from the melts made from the congruent composition charges, the compositions are characterised by the oxides mole ratio of 51.9% ($Lu_2O_3$+$Ce_2O_3$)/48.1% $SiO_2$ for the variant #1, the 51.9% ($Lu_2O_3$+$A_2O_3$+$Ce_2O_3$)/48.1% $SiO_2$ for the variant #2, the 51.9% ($Lu_2O_3$+$Li_2O$+$Ce_2O_3$)/48.1% $SiO_2$ for variant #3 and the 51.9% ($Lu_2O_3$+$Li_2O$+$A_2O_3$+$Ce_2O_3$)/48.1% $SiO_2$ for variant #4./

The specific peculiarities and the growth parameters of rare-earth silicates of stoichiometric composition for a directional crystallization method, in particular for Czochralski method are presented in article (C. D. Brandle, A. J. Valentino, G. W. Berkstresser "Czochralski growth of rare-earth orthosilicates ($Ln_2SiO_5$), J. Crystal Growth 79 (1986), pp. 308–315). In this paper a ratio of crystal diameter (d) to a crucible diameter (D) has a magnitude d/D=0.4, which is an optimal value for Czochralski method. A condition of optimal dimensions of crucible for Czochralski method is a crucible height (H) is equaled to its diameter, D=H.

The low temperature gradients are a key peculiarity of large (80 mm–150 mm in diameter) crystals growing by a directional crystallization method, in particular Kyropoulos method from the iridium crucibles of 100 mm–180 mm in diameter, and an optimal ratio of a crystal diameter to a crucible diameter is d/D=0.7–0.9. Kyropoulos method is widely utilized for a commercial production of massive sapphire crystals ($Al_2O_3$), and for some alkali-halide scintillation crystals also. However, the authors of given invention do not know publications about a growing of rare-earth silicates by Kyropoulos method. A technique and the attributes of Kyropoulos method and Czochralski method are described in detail in the book (K. T. Wilke "A growing of crystals" Leningrad, publisher <Nedra>, 1977, 600 p., a translation from German von K. Th. Wilke "Kristallzüchtungen", VEB Deutcher Verlag der Wissenschaften, Berlin, 1973).

The drawings of scintillation substances growth corresponding to the variants #1, #2, #3 and #4 by Kyropoulos method are presented at FIG. 2 and FIG. 3. A crystal growth is fulfilled from an iridium crucible 4, a large in cross-section a lutetium oxyorthosilicate crystal is used as a seed crystal 5, large cross-section dimension maintains a reliable start of crystal growth in the conditions of low temperature gradients and a strong light heating from an upper part of lateral crucible surface. At the beginning of crystal growth process a melt occupies only a part of crucible volume and $H_m$ is an optimal height of melt. At starting phase of crystal growth a cone 6 is growing and after shouldering a crystal 7 is being grown with a changeless diameter. A flow chart of crystal growth by Kyropoulos method for a case of 100% crystallized initial melt is shown on Fir. 2 A flow chart of crystal growth for a case of partly (70%–90%) crystallized melt, when small amount of unused substance 9 is left in a crucible, is presented on FIG. 3. The optimal values of a crucible diameter (D) and a height (H), an initial level of a melt in crucible ($H_m$), a crystal diameter (d) and length of cylindrical part of a crystal (h) are given by the relations:

$$h=H+y,$$

where y≈0.1 D; (d/D)≈0.7÷0.9; $H_m$≈$(d/D)^2$ h.

At the optimal ratio (d/D)≈0.8 a grown crystal is placed within a crucible during cooling, that is an important condition for uniform decreasing of temperature over boule volume during an after-growth annealing. Such placement of a crystal relative to a crucible is a principal difference between Kyropoulos method and Czochralski method, in which a grown crystal is placed above the crucible after breaking away of melt to start an annealing process. A different position of crystal relative to crucible in Czochralski method results in the conditions under which a top of grown boule has an appreciably lower temperature than a bottom placed near a hot crucible. This circumstance leads to a different content of oxygen vacancies and to a different $Ce^{3+}/Ce^{4+}$ ions ratio through the full crystal length, this is an additional cause of a strong spread of parameters from boule to boule grown by Czochralski method of the scintillating lutetium oxyorthosilicate crystals. All boules grown by Czochralski method have some differences of properties through the crystal length and its diameter, and in combination with annealing under the heavy temperature gradients this results in the considerable spread of parameters of scintillation elements fabricated from the different parts of boule. Contrariwise, the low temperatures gradients in a crystal during annealing process are achieved if a boule is placed within a crucible, as FIG. 2 and FIG. 3 demonstrates. Practically such method of fabrication allows to cool the crystals in the near isothermal conditions. This is a basis to achieve an invariability of light yield from the different parts of a large Kyropoulos grown crystal.

In the scintillation substance described in the variants #2, #4, #7 and #10 an isomorphic substitution of the lutetium ions for at least one of the ions of the group Gd, Sc, Y, La, Eu, and Tb, is possibly, at that a substitution may be fulfilled at a more wide range than it is claimed in the given invention. However a conceptual drawback of considerable widening of a lutetium ions substitution range is a decrease of crystal density and, consequently, a sharp decrease of efficiency of gamma-quantums absorption that results in a decreasing of light yield. Besides, the Eu and Tb ions decrease the luminescence intensity in the blue region of spectrum because a part of energy due to the redistribution emits in a red region of spectrum at europium substitution and emits in a green region of spectrum at terbium substitution. In a case of the properly chosen concentrations of the cerium, terbium, and europium ions a scintillation crystal emits a white light, i.e. all visible region of spectrum. The scintillation substances having such emission spectrum more effectively work with the semiconductor detectors, because the cheap silicon/germanium semiconductor detectors have the two-tree times less sensitive in a blue region of spectrum in comparison with green, and moreover red region of spectrum. A substitution of Lu ions for the optically inactive Gd, Sc, Y, and La ions allows to control a lattice parameter and to grow the crystals free from a mechanical stresses reducing a crystal cracking during an after growth annealing and a cutting. Besides, a partial substitution of an expensive lutetium for the cheap La, Gd, and Y reduces a cost of scintillation substance.

The ion radiuses of Y (1.016 Å), La (1.190 Å), Eu (1.073 Å), Gd (1.061 Å), Tb (1.044 Å) are appreciably larger than the Lu (0.72 Å) ion radius. At interaction of gamma-quantum with a lattice a formation of the numerous quantity of free electrons and the holes, wherefrom these electrons were taken out by gamma-quantum, takes place. In consequent recombination of electrons with holes an excitation of lattice occurs, this energy transfers to the cerium ions which emit in blue range of spectrum. Specially a recombination is effective on the optical centers where the atoms having the very distinguishing radiuses are besides. For example, a substitution of part of lutetium ions for the lanthanum ions having significantly larger diameter results in a sharp light yield increasing, that will be proved in the examples of substances confirmatory the given invention. In order to an electron-hole recombination has a maximal effect the use of small concentrations of the isomorphic substituting dopants is required. At large concentrations a concentration quenching occurs and an efficiency is decreased, this lead to reducing of light yield. On the basis of the above reasoning and the experimental data, the range of variable z is chosen between $1 \times 10^{-4}$ f. units and 0.05 f. units for the variants of the substances $Ce_xLu_{2+2y-x-z}A_zSi_{1-y}O_{5+y}$ and $Ce_xLi_{q+p}Lu_{2-p+2y-x-z}A_zSi_{1-y}O_{5+y-p}$, where A is at least one elements of the group Gd, Sc, Y, La, Eu, and Tb. However, this range may be extended appreciably for the Y and La elements, for which an enlarged light yield is maintained even at the high concentrations while the crystal density is decreasing. Thus a technical result in the specific forms of implementations is achieved due to a growing of scintillation substance of $Ce_xLu_{2.076-x-m-n}La_mY_nSi_{0.962}O_{5.038}$, in which the value of variable m does not exceed 0.05 f. units, and the range of variable n is between $1 \times 10^{-4}$ f. units and 2 f. units.

For the substances of the #6 and #10 variants having the chemical formulae $Ce_xLi_{q+p}Lu_{9.33-x-p-z}{}^{\perp}{}_{0.67}A_zSi_6O_{26-p}$ and $Ce_xLi_{1+q+p}Lu_{9-x-p-z}A_zSi_6O_{26-p}$, accordingly, a range for variable z is set between $1 \times 10^{-4}$ f. units and 8.9 f. units. To maintain a large density and a high light yield the small concentrations are preferable as said the above. Nevertheless, an upper limit is set at 8.9 f. units, in this case the crystals have a low density and a comparatively small light yield with a sharp decreasing of an initial chemicals cost and, therefore, a crystal cost. Such crystals may be interest for utilization as the sensors in the atomic power plants for which the important parameters are a high radioresistance and chemical resistance in the compatibility with a low cost. The similar sensors should be in every room of plant to measure a radiation level without presence of human. The existent sensors on the basis of alkali-halide crystals are unreliable because they cannot operate in a high radiation level possible in case of the emergencies.

For the #3 and #4 variants of scintillation substance on the basis of lutetium silicate, a common distinctive feature is a presence of the lithium ions in the quantity does not exceeding 0.25 f. units, at that the lithium is placed in the interstitial sites of crystal lattice in the quantity of q formula units, another part of lithium ions are placed in the sites of the lattice substituting the lutetium ions in the quantity of p formula units. The positive effect of intercalation of the lithium ions into the interstitial sites of structure is achieved due to (a) an intercalation is followed by the minimal change in a crystal structure of substance;

(b) an intercalation of the lithium ions gives rise to a formation of the reduced phases of $Li_qCe$, i.e. a presence of the lithium ions in the scintillation substances of $Ce_xLi_{q+p}Lu_{2-p+2y-x}Si_{1-y}O_{5+y-p}$ and $Ce_xLi_{q+p}Lu_{2-p+2y-x-z}A_zSi_{1-y}O_{5+y-p}$ promotes to a stabilization of cerium ions in the $Ce^{3+}$ valence state, that appreciably increases a light yield;

(c) an intercalation of the lithium ions gives rise to the change of a conduction (A. A. Veshman, K. I. Petrov, "A functional inorganic lithium compounds" Moscow, Energoizdat, (1996), 208 p.), that decreases an afterglow time of substance, TABLE 1.

For the #3 and #4 variants of substances, the lower p and q boundaries for a content of lithium are set to be equaled to $1 \times 10^{-4}$ f. units, because this is the limit of lithium content when the effect of a decreasing of afterglow and the effect of increasing of light yield are possibly to observe. The upper limit of the content of lithium in scintillation substance is determined by experimentally, at the total content of lithium ions exceeding 0.25 f. units a light yield intensity falls sharply due to a conduction of substance excessively rises and such scintillation substance becomes inapplicable to the industrial applications for its direct purpose—for the registration of x-ray, gamma and alpha radiation, TABLE 1.

All scintillation substances on the basis of silicate claimed in the #1 to #4 variants, inclusively, refer to a monoclinic syngony, a spatial group B2/b. The scintillation substances on the basis of silicate claimed in the fifth to tenth variants, inclusively, belong to another structural type, namely, apatite-brytolite with a spatial group P6$_3$/m, Z=1. The substances claimed in the #6 and #7 variants have an important common distinctive feature, namely, they contain the lithium ions of the total quantity (p+q) does not exceeding 0.55 f. units, where q denotes a quantity of lithium intercalated in the interstitial sites, p denotes a quantity of the lithium substituting the rare-earth ions. The upper limit of q equaled up to 0.3 f. units is determined by experimentally. When the quantity of lithium intercalated is above the indicated limit, the destruction of the structural type P6$_3$/m and the formation of inclusions of other phases takes place, which determine the scattering of light and the decrease of transparency of a scintillating crystal. The upper limit of p equaled to 0.25 f. units is determined by the fact that an apatite-similar structure is retained at the substitution of the rare-earth atoms for lithium only for case, when a substitution of rare-earth atoms placed in the large nine-coordinated sites occurs, because only such sites let a distortion and a deviation from an ideal symmetry. With this the seven-coordinated sites, the second position for rare-earth ions in the structure, are always occupied by the rare-earth elements. The lower boundaries for the contents of lithium ions p and q are determined by the fact that at the quantity lower than the $5\times10^{-4}$ f. units limit a technical result, lying in increasing of the light yield and decreasing of the afterglow of scintillation, cannot be reached.

For the variants #9 and #10 the upper limit of the content of lithium is determined to 1.55 f. units, because apatite-brytolite structure remains a stable over a wide substitution range of elements of first position for the lithium ions. A substitution of large quantity of the basic-forming cerium ions for lutetium and cerium both in the mono-cation and double cerium silicates, being the analogues, lets to decrease the quenching effect of cerium luminescence and new substance obtains the scintillation properties.

Our experimental researches showed that the crystals of $Ce_xLiR_{9-x}Si_6O_{26}$, and $R_{9.33}\square_{0.67}Si_6O_{26}$, where R=La, Gd, grown by Czochralski method have a high optical quality, however they are behind the lutetium oxyorthosilicate crystals both in a density and in a light yield. To improve the most important scintillation parameters we have grew the following crystals: $Ce_{0.015}LiGd_{2.985}Lu_6Si_6O_{26}$; $Ce_{0.015}LiLa_{2.985}Lu_6Si_6O_{26}$; $Ce_{0.015}LiGd_{5.985}Lu_3SiO_6O_{26}$; $Ce_{0.015}LiLu_{8.985}Si_6O_{26}$, $Ce_{0.015}Li_{0.45}Lu_{8.935}Si_6O_{26}$, $Ce_{0.015}Li_{0.12}Gd_{2.985}Lu_{6.33}\square_{0.67}Si_6O_{26}$, $Ce_{0.015}Li_{0.33}Eu_{1.985}Lu_{6.3}\square_{0.67}Si_6O_{26}$, $Ce_{0.015}Li_{0.25}Gd_{2.985}Lu_{6.28}\square_{0.67}Si_6O_{26}$, $Ce_{0.011}Li_{0.25}Y_{6.989}Lu_{2.23}\square_{0.67}Si_6O_{25.9}$, $Ce_{0.011}Li_{0.35}Y_{3.989}La_{0.9}Lu_{3.33}\square_{0.67}Si_6O_{25.9}$, $Ce_{0.12}Li_{0.05}La_{3.988}Lu_{5.33}\square_{0.67}Si_6O_{26}$. The numerous experiments with different growth conditions let to obtain this substances in the polycrystalline forms only. The testing of polycrystal of the $Ce_{0.015}LiLu_{8.985}Si_6O_{26}$ composition shows that this new scintillation substance has near a density, a light yield and a decay time, to the known Ce:LSO crystal To determine the boundaries of composition of scintillation substances of the variants #6 and #7 which possibly to grow in the form of single crystal we have tested the substances having an initial composition of melt: $Ce_{0.012}Li_{0.1}Lu_{5.33}La_{3.988}\square_{0.67}Si_6O_{26}$; $Ce_{0.012}Li_{0.2}Lu_{2.33}La_{6.988}\square_{0.67}Si_6O_{26}$; $Ce_{0.012}Li_{0.1}Lu_{5.33}La_{3.988}\square_{0.67}Si_6O_{26}$; $Ce_{0.015}Li_{0.45}Lu_{2.115}Gd_7\square_{0.67}Si_6O_{25.8}$; $Ce_{0.015}Li_{0.1}Lu_{7.31}Y_2\square_{0.67}Si_6O_{25.95}$; $Ce_{0.015}Li_{0.28}Lu_{7.815}Eu_{1.5}\square_{0.67}Si_6O_{26}$. All these compositions were obtained in the forms of the single crystals, or the translucent, or the white nontransparent polycrystal ingots. For example, the use of a melt of the $Ce_{0.015}Li_{0.56}Lu_{1.065}La_8\square_{0.67}Si_6O_{25.75}$ chemical composition and at the 2.5 mm/hour pulling rate of growing crystal allows to grow from this melt the crystal of the $Ce_{0.003}Li_{0.55}Lu_{1.327}La_8\square_{0.67}Si_6O_{26}$ chemical composition. The increasing of pulling rate and gradients on the melt-crystal interface allows to obtain the new crystalline scintillation substances over the range of compositions from $Ce_{0.003}Li_{0.55}Lu_{1.077}La_8\square_{0.67}Si_6O_{25.75}$ to $Ce_{0.015}Li_{0.55}Lu_{1.065}La_8\square_{0.67}Si_6O_{25.75}$. In a generalized form this new scintillation substance (the variants #6 and #7) has the following chemical formula: $Ce_xLi_{q+p}Lu_{9.33-x-p-z}A_z\square_{0.67}Si_6O_{26-p}$, where the variables q and p does not exceed a value of 0.3 f. units and 0.25 f. units, respectively, a variable z is changed within the limits from $5\times10^{-4}$ f. units to 8.9 f. units.

To determine the boundaries of compositions of scintillation substances which possibly to grow in the form of a single crystal according to the #9 and #10 variants, the following substances of an initial composition of melt were tested: $Ce_{0.015}LiLu_{8.985}Si_6O_{26}$; $Ce_{0.015}Li_{1.55}Lu_{8.735}Si_6O_{25.75}$; $Ce_{0.015}Li_{1.05}Lu_{8.985}Si_6O_{26}$; $Ce_{0.015}Li_{1.3}Lu_{1.785}La_7Si_6O_{25.8}$; $Ce_{0.015}Li_{1.4}Lu_{6.885}Y_2Si_6O_{25.9}$; $Ce_{0.015}Li_{1.2}Lu_{2.885}Gd_6Si_6O_{25.9}$. All these compositions were obtained in the form of single crystals or the translucent, or the white nontransparent polycrystal ingots. For example, the use of a melt of the $Ce_{0.015}LiLu_{8.997}Si_6O_{26}$ chemical composition and at the 0.5 mm/hour pulling rate of growing crystal allows to grow from this melt the single crystal of the $Ce_{0.003}LiLu_{8.997}Si_6O_{26}$ chemical composition. The increasing of pulling rate and gradients on the melt-crystal interface allows to obtain the new crystalline scintillation substances over the range of compositions from $Ce_{0.003}LiLu_{8.997}Si_6O_{26}$ to $Ce_{0.015}Li_{1.55}Lu_{8.735}Si_6O_{25.75}$. In a generalized form this new scintillation substance (the variants #9 and #10) has the following chemical formula: $Ce_xLi_{1+q+p}Lu_{9-x-p}A_zSi_6O_{26-p}$, where the variables q and p does not exceed a value of 0.3 f. units and 0.25 f. units, respectively, a variable z is changed within the limits from $5\times10^{-4}$ f. units to 8.9 f. units.

We executed a sciagram analysis of the powdered $Ce_xLi_{q+p}Lu_{9-x-p}Si_6O_{26-p}$ crystal samples using X-ray diffractometer. The analysis showed that the $Ce_xLi_{q+p}Lu_{9-x-p}Si_6O_{26-p}$ single crystals being crystallized in a hexagonal syngony and may be classified to an apatite-brytolite structural type with a spatial group P6$_3$/m, Z=1. The indexing X-ray diffraction pattern of the $Ce_{0.003}LiLu_{8.997}Si_6O_{26}$ crystal is presented on FIG. 4. Taking into account all 35 reflects from the planes at the 2θ angles of reflection over the range from 15 degrees to 60 degrees, we calculated the lattice cell parameters which are equaled to a=11.66 Å and c=21.58 Å.

The measurements of crystals density were carried out according to a standard procedure of hydrostatic weighing, this method is utilized in geology during ten-years. In these experiments we used the bulk polished samples weighing about 8–15 grams. The measurements were fulfilled in a distilled water preliminary boiled during 20 minutes to remove an oxygen and cooled to the room temperature. A temperature of water was being measured with an accuracy 0.1° C. To provide the minimal errors, each sample was weighed five times, in this case an error of determination of crystal samples density did not exceed 0.001 gram/cm³. The results of the measurements are presented in TABLE 1.

An experimental study of dependence of scintillation decay time and a light yield in the 410–450 nm range of spectrum on chemical composition of crystals was carried out utilizing an emission of radionuclide $^{60}$Co as described in the article (E. G. Devitsin, V. A. Kozlov, S. Yu. Potashov, A. I. Zagumennyi, Yu. D. Zavartsev "Luminescent properties of $Lu_3Al_5O_{12}$ crystal doped with Ce" Proceeding of International Conferences "Inorganic scintillators and their applications" (SCINT 95), Delft, the Netherlands, Aug. 20–Sep. 1, 1995). The results of the measurements are presented in TABLE 1.

The measurements of a luminescence intensity and a time of an afterglow were fulfilled with the polished samples of 8–15 grams weight. The intensity and afterglow of reference sample were the same after the gamma-radiation and ultraviolet (UV) radiation exposures, so for the systematic measurements the UV-excitation set was used. A luminescence of the samples was excited by the standard 12 W UV-lamp during the 60 minutes exposure, after the switching-out of the lamp a fluorescence decreasing was recorded during 120 minutes with a photomultiplier FEU-100 or a photodetector FD-24K connected with oscilloscope Tektronix TDS 3052 or multimeter Agilent 34401A lined with computer. A variation of intensity of the samples having a strong afterglow effect are characterized by an exponential dependence having a time constant about 25–35 minutes, these samples maintain a strong fluorescence during more than the 180 minutes. The samples having a low afterglow effect are characterized by the dependence having a time constant about several decades seconds. For some samples an afterglow effect was not observed after switching-out of the lamp. The results of the afterglow effect measurements for the different samples are presented in TABLE 1.

BRIEF DESCRIPTION OF THE DRAWING

The essence of proposed technical solutions is illustrated by the following drawings.

Figure 1:
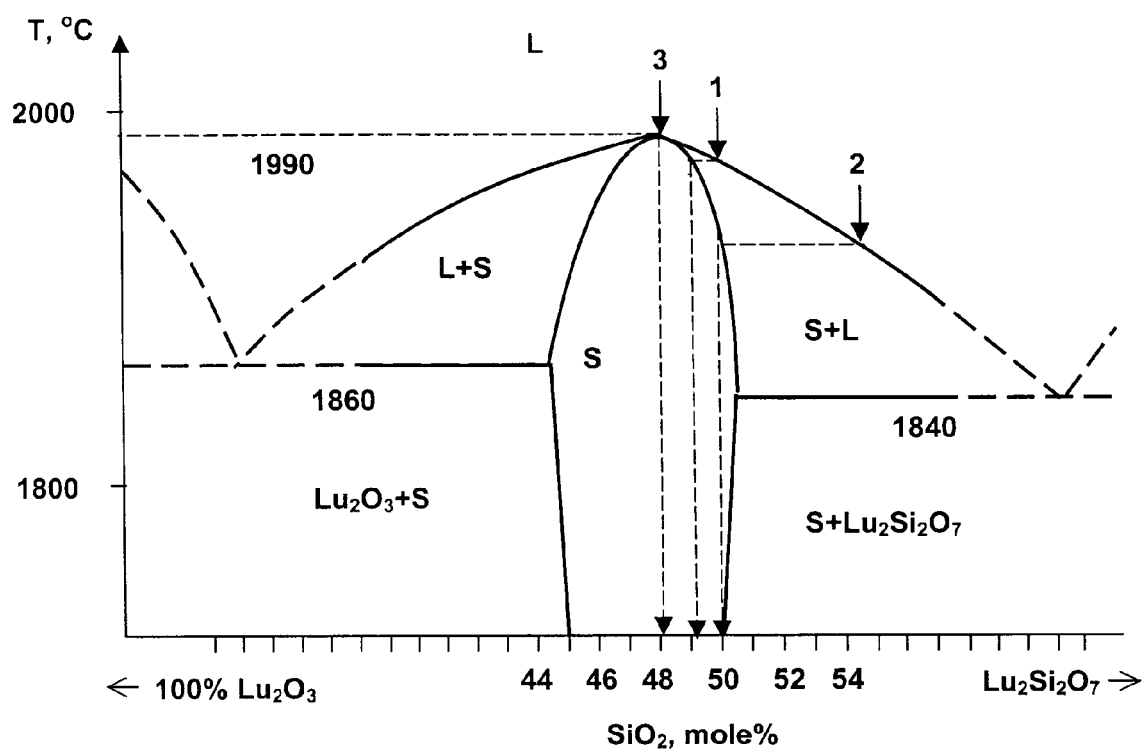
FIG. 1 depicts the fragment of phase diagram of $Lu_2O_3$—$SiO_2$ system.
Figure 2:
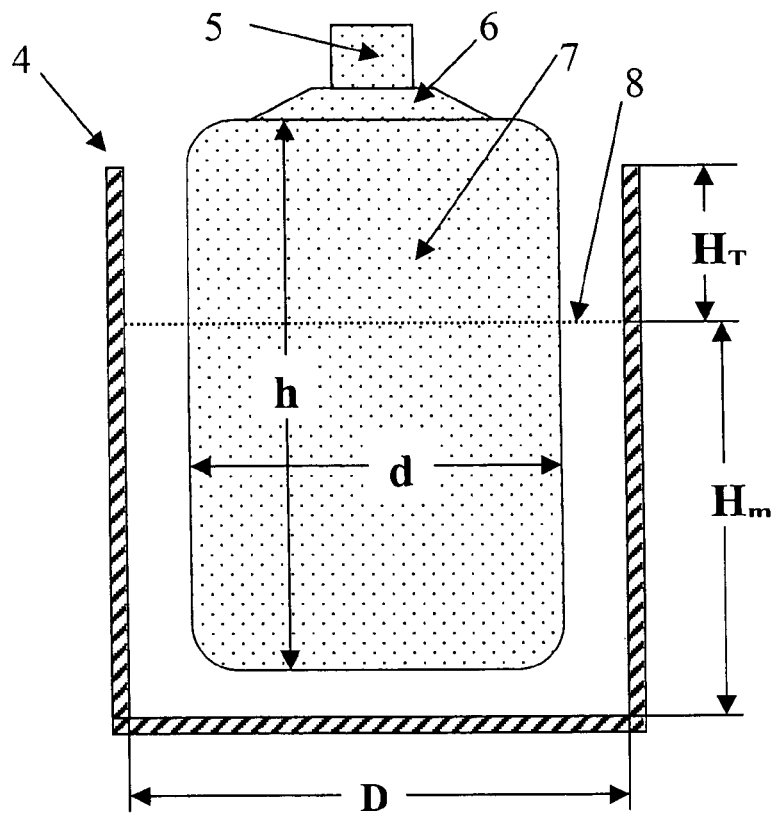
FIG. 2 shows the scheme of the optimal dimensions of a crystal and crucible for a case of crystal growth by Kyropoulos method.
Figure 3:
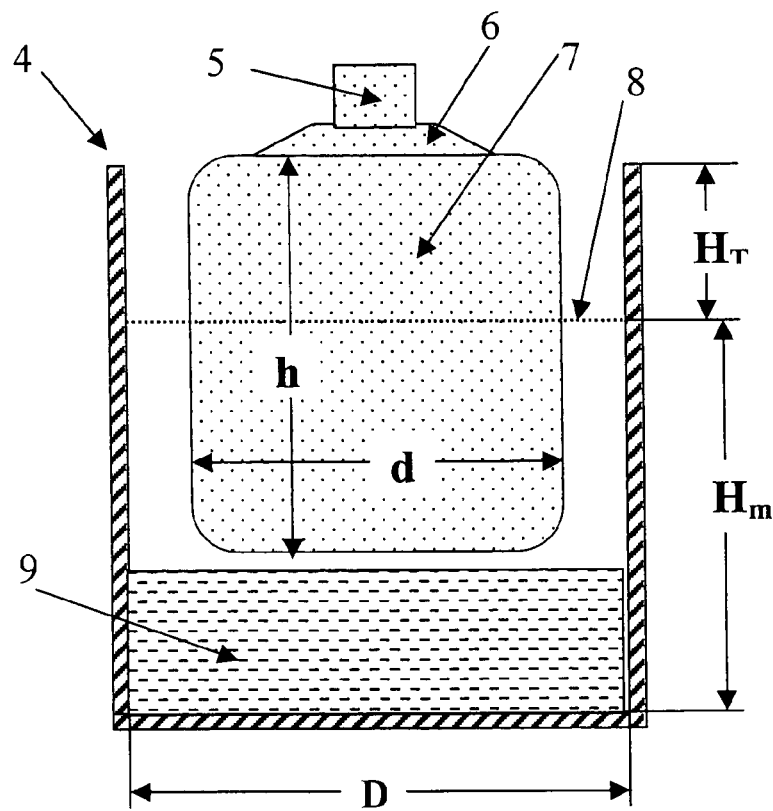
FIG. 3 depicts a flow chart of crystal growth by Kyropoulos method for a case of partly crystallized melt.
Figure 4:
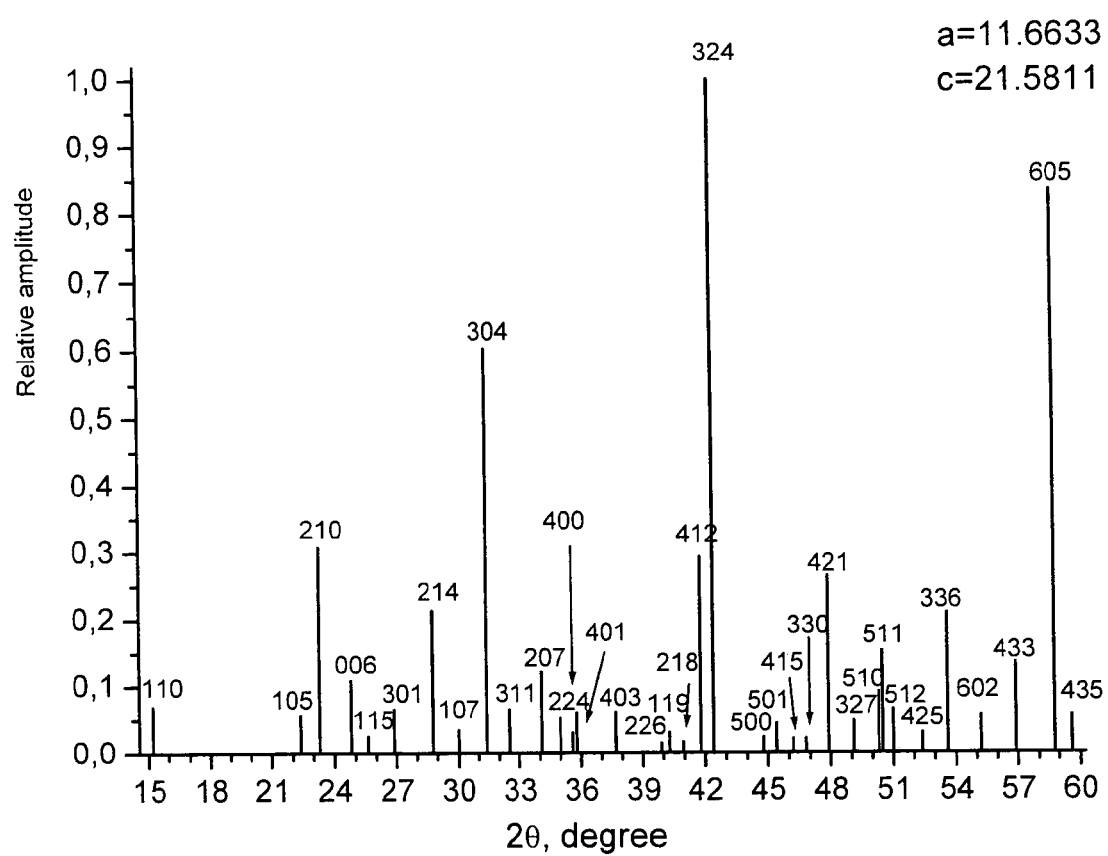
FIG. 4 shows the X-ray powder diffraction pattern of $Ce_{0.003}Li_{1.08}Lu_{8.947}Si_6O_{25.95}$ crystal.

All crystals fabricated and examined during the fulfilment of the given invention were grown from the iridium crucibles, the chemicals with the extra-purity of 99.99% and 99.999% were used as the source reagents.

DETAILED DESCRIPTION OF THE INVENTION

TABLE 1 shows the results of testing of the synthesised scintillating substances. The values of the light yields, the decay times of scintillation, the afterglow times, the densities, the atomic numbers ($Z_{eff}$) are compared for different compounds. The values of light yield are presented in units relative to a light yield of "the reference" $Ce_{0.0024}Lu_{1.998}SiO_5$ sample (the Ce:LSO prototype crystal).

TABLE 1

Comparison of scintillating characteristics of the scintillation substances of different compositions.

| Compositions of substances | Decay time (ns) | Light yield, (relative units) | After glow presence (relative units) | Density (gram/cm³) | Luminescence range (nm) | Atomic number $Z_{eff}$ |
|---|---|---|---|---|---|---|
| $Ce_{0.0024}Lu_{1.998}SiO_5$ | 43.3 | 1.0 | 1.0 | 7.406 | 415–430 | 63.8 |
| $Ce_{0.001}Lu_{2.075}Si_{0.962}O_{5.038}$ | 44.5 | 1.05 | 1.0 | 7.409 | 420–440 | 64.0 |
| $Ce_{0.002}Lu_{2.074}Si_{0.962}O_{5.038}$ | 43.4 | 1.0 | 0.8 | 7.408 | 420–440 | 64.0 |
| $Ce_{0.0015}Lu_{2.0445}Tb_{0.03}Si_{0.962}O_{5.038}$ | 34.2 | 0.33 | 1.0 | 7.399 | 420–440 535–550 | 64.0 |
| $Ce_{0.0015}Lu_{2.0645}Tb_{0.005}Eu_{0.005}Si_{0.962}O_{5.04}$ | 34.7 | 0.32 | 1.05 | 7.406 | 420–440 535–550 620–635 | 64.0 |
| $Ce_{0.0025}Lu_{2.0685}Y_{0.005}Si_{0.962}O_{5.038}$ | 42.7 | 1.09 | 0.9 | 7.403 | 425–445 | 64.0 |
| $Ce_{0.0025}Lu_{2.0685}Sc_{0.005}Si_{0.962}O_{5.038}$ | 41 | 0.95 | 0.8 | 7.403 | 420–440 | 64.0 |
| $Ce_{0.0025}Lu_{2.0685}La_{0.005}Si_{0.962}O_{5.038}$ | 43 | 1.12 | 0.8 | 7.404 | 430–450 | 64.0 |
| $Ce_{0.0025}Lu_{2.049}La_{0.02}Si_{0.962}O_{5.038}$ | 44.1 | 1.27 | 0.9 | 7.394 | 430–450 | 63.9 |
| $Ce_{0.003}Li_{0.005}Lu_{2.049}La_{0.02}Si_{0.962}O_{5.038}$ | 41.3 | 1.38 | 0.9 | 7.393 | 430–450 | 63.9 |
| $Ce_{0.02}LiLu_{8.98}Si_6O_{26}$ | 36 | 0.8 | 0.7 | 7.314 | 415–430 | 62.6 |
| $Ce_{0.015}LiLu_6Gd_{2.985}Si_6O_{26}$ | 35.2 | 0.4 | No | 7.012 | 420–440 | 60.6 |
| $Ce_{0.015}Li_{0.45}Lu_{8.935}Si_6O_{25.65}$ | 36 | 0.9 | 0.2 | 7.331 | 415–430 | 62.6 |
| $Ce_{0.015}LiLu_6La_{2.985}Si_6O_{26}$ | 38 | 1.4 | 0.3 | 6.701 | 420–440 | 59.1 |
| $Ce_{0.003}LiLu_{8.997}Si_6O_{26}$ | 39.7 | 1.2 | 0.3 | 7.318 | 415–430 | 62.6 |
| $Ce_{0.003}Li_{1.08}Lu_{8.947}Si_6O_{25.97}$ | 39 | 1.2 | 0.3 | 7.310 | 415–430 | 62.6 |
| $Ce_{0.015}Li_{1.55}Lu_{8.735}Si_6O_{25.9}$ | 35 | 0.75 | 0.2 | 7.270 | 415–430 | 62.6 |
| $Ce_{0.015}LiLu_3Gd_{5.985}Si_6O_{26}$ | 31 | 0.3 | No | 6.691 | 430–440 | 58.3 |
| $Ce_{0.001}Li_{1.2}Lu_{3.698}Gd_{5.1}Si_6O_{26.1}$ | 34 | 0.35 | No | 6.784 | 430–440 | 59.0 |
| $Ce_{0.04}Li_{1.2}Lu_{8.66}Eu_{0.2}Si_6O_{25.95}$ | 33 | 0.25 | 0.2 | 7.285 | 420–440 620–635 | 62.3 |
| $Ce_{0.1}Li_{1.2}Lu_{7.9}Y_{0.7}Tb_{0.1}Si_6O_{25.8}$ | 28 | 0.35 | 0.2 | 7.095 | 420–440 535–550 | 61.3 |
| $Ce_{0.002}Li_{1.45}Lu_{6.298}Y_{2.5}Si_6O_{25.93}$ | 42 | 1.1 | 0.5 | 6.645 | 425–445 | 58.3 |

TABLE 1-continued

Comparison of scintillating characteristics of the scintillation substances of different compositions.

| Compositions of substances | Decay time (ns) | Light yield, (relative units) | After glow presence (relative units) | Density (gram/cm$^3$) | Luminescence range (nm) | Atomic number $Z_{eff}$ |
|---|---|---|---|---|---|---|
| $Ce_{0.0015}Li_{1.3}Lu_{8.3985}La_{0.5}Si_6O_{26}$ | 42 | 1.2 | 0.5 | 7.198 | 430–450 | 62.0 |
| $Ce_{0.015}Li_{0.1}Lu_{6.33}Gd_{2.985}\square_{0.67}Si_6O_{26.06}$ | 32 | 0.4 | No | 7.083 | 430–440 | 61.0 |
| $Ce_{0.015}Li_{0.33}Lu_{7.3}Eu_{1.985}\square_{0.67}Si_6O_{26.1}$ | 34.5 | 0.09 | No | 7.019 | 420–440 620–635 | 61.4 |
| $Ce_{0.015}Li_{0.25}Lu_{6.28}Gd_{2.985}\square_{0.67}Si_6O_{26.05}$ | 36 | 0.5 | No | 7.073 | 430–440 | 60.9 |
| $Ce_{0.011}Li_{0.2}Lu_{2.23}Y_{6.989}\square_{0.67}Si_6O_{25.95}$ | 41 | 1.0 | 0.7 | 5.261 | 425–445 | 46.6 |
| $Ce_{0.011}Li_{0.1}Lu_{3.33}Y_{5.989}\square_{0.67}Si_6O_{26}$ | 44 | 1.4 | 1.0 | 5.749 | 425–445 | 51.0 |
| $Ce_{0.012}Li_{0.05}Lu_{5.33}La_{3.988}\square_{0.67}Si_6O_{26}$ | 44 | 1.2 | 1.0 | 6.570 | 430–450 | 58.3 |
| $Ce_{0.003}Li_{0.55}Lu_{1.077}La_8\square_{0.67}Si_6O_{25.9}$ | 41 | 0.8 | No | 5.549 | 430–450 | 51.4 |

EXAMPLE 1

Growth of known a "reference" $Ce:Lu_2SiO_5$ crystal having the Lu/Si=2 ratio, and also the growing of crystal having a ratio of formula units of (Lu+Ce)/Si=2.061 (y=0.015), which is out of compositions range of variant No1 of given invention.

Due to a strong data spread about the crystal parameters published in the different issues, the parameters of commercial $Ce:Lu_2SiO_5$ crystals may be accepted as the most reliable data. The higher light output is demonstrated by the LSO crystals, having a concentration of cerium ions equaled to 0.12 at. % (or about 0.002 f. units), the chemical formula of reference crystal is $Ce_{0.002}Lu_{1.998}SiO_5$. Taking into account that the segregation coefficient of the cerium ions between a melt and growing crystal is equaled about k=0.2, it is needed to charge a crucible with the starting material having a cerium concentration about 0.6 at. % (or in the formula units: 0.012 f. units). A ratio of the $Lu_2O_3$ and $SiO_2$ oxides should be calculated taking into account the peculiarities of a directional crystallization method (Czochralski method, Stepanov's method, the Bridgman method or any other method of a directional crystallization). We have grew the "reference" $Ce:Lu_2SiO_5$ crystals by Czochralski method in the conditions of low temperature gradients (Experiment #1) and in conditions of high temperature gradients (Experiment #2 and #3).

Experiment #1. (The non-equilibrium conditions, charge composition of 50% $(Lu_2O_3+Ce_2O_3)$/50% $SiO_2$). A growing of crystal was carried out from an iridium crucible of the 40 mm in diameter under a weak thermal insulation in protective argon atmosphere (100% volume of argon), at pulling rate of 3.5 mm h$^{-1}$, rotation rate of 15 r.p.m. The initial charge of a melt had a composition described by a chemical formula of $Ce_{0.012}Lu_{1.998}SiO_5$. In these conditions a crystal approximately 16 mm in diameter and 54 mm length was grown, a top of boule was colourless and did not have the fine scattering inclusions, but a bottom of boule had the cracks. The content of cerium, lutetium and silicon ions was determined in crystal by electron microprobe analysis using the commercial Cameca Camebax SX-50 spectrometer. A composition of top conical part of the crystal is characterised by the chemical formula of $Ce_{0.002}Lu_{1.998}SiO_5$, having ratio of (Lu+Ce)/Si equaled exactly to 2, that is possible in the conditions of crystallisation far from the equilibrium. However in the bottom of crystal the ratio of (Lu+Ce)/Si becomes less than 2. For fabrication of "reference" sample the top of conical part of the boule was used. The parameters of "reference" sample are presented in TABLE 1.

Experiment #2. (The equilibrium conditions, charge composition of 50% $(Lu_2O_3+Ce_2O_3)$/50% $SiO_2$). A growing of crystal was executed from an iridium crucible of the 40 mm in diameter under a good thermal insulation conditions in a protective argon atmosphere (99.5% volume of argon and 0.5% volume of oxygen), at pulling rate of 2 mm h$^{-1}$, rotation rate of 15 r.p.m. The initial charge of a melt had a composition described by a chemical formula of $Ce_{0.012}Lu_{1.998}SiO_5$. In these growth conditions the crystal approximately 18 mm in diameter and 45 mm length was grown, the crystal did not contain the fine scattering inclusions and was a colourless. The content of cerium, lutetium and silicon ions was determined in crystal by electron microprobe analysis using the commercial spectrometer. A composition of top conical part of the crystal is characterised by the chemical formula of $Ce_{0.003}Lu_{2.027}Si_{0.985}O_{5.015}$, having ratio of (Lu+Ce)/Si=2.061. To the bottom of crystal the concentration of cerium ions is being increased, and ratio of (Lu+Ce)/Si becomes a lower than 2.061. Obviously, that such crystal cannot be used as a "reference" sample, because its composition is differed from composition of know $Lu_{2-x}Ce_xSiO_5$ crystal.

Experiment #3. (Charge composition is 46% $(Lu_2O_3+Ce_2O_3)$/54% $SiO_2$). A growing of crystal was executed from an iridium crucible of the 40 mm in diameter under a good thermal insulation in a protective atmosphere (99.5% volume of argon and 0.5% volume of oxygen), at pulling rate of 2 mm h$^{-1}$, rotation rate of 15 round per minutes (r.p.m). In accordance with a composition is denoted by an arrow 2 of FIG. 1 it is needed to use the original charge composition of 46%$(Lu_2O_3+Ce_2O_3)$/54%$SiO_2$, which corresponds to a melt having the $Ce_{0.012}Lu_{1.828}Si_{1.080}O_{4.920}$ chemical composition. In these conditions the crystal 52 mm in length and 16 mm diameter was grown. The crystal was colourless, but it included the fine scattering inclusions, an amount of which was increased from a top to a bottom of a boule. The content of cerium, lutetium and silicon ions was determined in a top part of crystal by electron microprobe analysis using the commercial spectrometer. A composition of the crystal is within the compositions range between the $Ce_{0.0022}Lu_{1.997}Si_{1.0}O_5$ (a top part of a boule) and the $Ce_{0.0028}Lu_{1.968}Si_{1.010}O_{4.98}$ (a bottom part of boule).

A comparison of scintillation parameters of couple of samples, fabricated in the experiments #1 and #3, had shown, that they have approximately identical light output under gamma excitation, and both samples demonstrated approximately the same decay time τ=43 ns.

EXAMPLE 2

A confirmation of the invention in the particular forms of implementation—the method of making of scintillation substances. To grow a large single crystal by Kyropoulos method according with the variants #1, #2, #3, and #4, an optimal scintillation substance having a composition of charge characterised by an oxides mole ratio of 51.9% $(Ce_2O_3+Lu_2O_3+A_2O_3+Li_2O)/48.1\%$ $SiO_2$ was chose. At such oxides ratio, the compositions of a melt and of a crystal are characterised by a chemical formula of $Ce_xLi_{q+p}Lu_{2.076-p-x-z}A_zSi_{0.962}O_{5.038-p}$, where A is at least one element selected from the group consisting of Gd, Sc, Y, La, Eu, Tb, x is a value between $1\times10^{-4}$ f. units and 0.02 f. units, z is a value not exceeding 0.05 f. units, q+p is a value not exceeding 0.025 f. units.

The growing of crystal 78 mm in diameter was executed from iridium crucible of 96 mm in inner diameter and about 112 mm height using the computer-controlled installation equipped with a weighing system of growing crystal. Placed in an optimal thermal insulation crucible was filled with the mixed chemical reagents, a crystal growing was carried out in a flowing protective nitrogen atmosphere (99.7% volume of nitrogen with 0.3% volume of oxygen). A weight of starting charge of crucible was 4400 grams. An initial charge had a chemical composition $Ce_xLu_{2.076-x}Si_{0.962}O_{5.038}$, characterised by the oxides mole ratio of 51.9% $(Lu_2O_3+Ce_2O_3)/48.1\%$ $SiO_2$. The single crystal rod of $12\times12$ mm$^2$ section was used as a seed crystal. The pulling rate of crystal boule was being changed from 1 mm/hr to 8 mm/hr at the different stages of process. The shouldering of crystal from the seed size until diameter size of approximately 75–78 mm was accomplished along crystal length from 5 mm to 25 mm, after that the boule was grown at constant cylindrical diameter of 75–78 mm. The finishing of growth was carried out by means of increasing of pulling rate when the boule weight achieved the desired value of about 90% of charge (the crystallized melt fraction is 90%). The moment of breaking off of a crystal from a melt was fixed by the weighing system. An annealing and a cooling of crystal to room temperature was being carried out during 30 hours. Grown at these conditions crystal had 3910 grams in a weight of and 12.5 cm length. Due to such technology, the effect of crucible bloat is eliminated. The enlarge/distension of iridium crucible during cooling of melt occurred if the amount of residual melt is occupied more than 20% of crucible volume. The enlarge and bloat of crucible sharply decreases a life time of very expensive iridium crucible, and, therefore, the production cost of a crystal boule is being increased.

An obtained crystal boule was used for measurement of percentage loss of crystalline materials after a slicing, a sawing of boule into the thin elements, a screening and rejection of debris, the broken elements and elements having the small cracks. The second kind of losses depend on a thickness of diamond saws, however these losses easy to calculate taking into account a thickness of a saw, so they do not considering in given example.

The sawing of boule at the packs of 78 mm in diameter and 11 mm length was fulfilled by the diamond saw with the inner cutting edge having the thickness of 0.6 mm. After this stage was obtained the 9 slabs, which had not the cracks and spalls. At this stage of fabrication the losses was 0%. During the second stage the packs were cut in perpendicular direction into the plats of 1 mm thickness, a diamond saw with inner cutting edge of 0.2 mm thickness was used. In a result of cracks the losses were ~1%. In next stage the plats were glued together and cut into the rods with size of $1\times1\times11$ mm$^3$. In result of cracks the losses achieved ~3%. In the final stage the rods were glued into the blocks containing approximately $30\times30$ rods in each, the blocks were mechanically polished from one or both faces of scintillating elements. During this processing the losses were no more than 0.1%. Thus, in a result of cracks the total losses achieved about 4%.

For comparison the known Ce:$Lu_2SiO_5$ crystal 50 mm in diameter and 105 mm length was grown by Czochralski method using a crucible 100 mm in diameter and 100 mm height, the crystal was grown from a melt of initial composition characterised by chemical formula $Ce_{0.012}Lu_{1.998}SiO_5$. After the cutting of boule at the packs 50 mm in diameter and 11 mm length the cracks were observed in volume of 3 slabs from total 8 slabs. During fabrication of rods with size $1\times1\times11$ mm$^3$ having one mechanically polished face the losses of crystalline material in a result of cracks and spalls achieved totally about 32%.

The same technological scheme was used for a growing and a cutting of the crystals having compositions: $Ce_xLi_{0.08}Lu_{2.026-x}Si_{0.962}O_{5.008-p}$, $Ce_xLi_{0.02}Lu_{2.072-x}Si_{0.962}O_{5.034}$, $Ce_xLu_{2.066-x-z}La_{0.01}Si_{0.962}O_{5.038}$, $Ce_xLu_{2.036-x}Y_{0.04}Si_{0.962}O_{5.038}$, $Ce_xLi_{0.2}Lu_{2.006-x}Gd_{0.04}Si_{0.962}O_{5.018}$, $Ce_xLi_{0.15}Lu_{2.071-x-z}Tb_zSi_{0.962}O_{4.988}$, with a different content of cerium, x is a value between $1\times10^{-4}$ f. units and 0.02 f. units.

The chemical compositions of the melts offered in the given invention and a growing of crystals by Kyropoulas method allow sharply to reduce the losses of crystalline scintillation material in the stages of cutting of large boules.

EXAMPLE 3

Method of making of the scintillation substances in form of scintillating ceramics on the basis of lanthanum and lutetium oxyorthosilicate differed in that the mixture of chloride water solution of Lu, La, Ce and liquid of $SiCl_4$, are used as a starting material for preparation of charge of composition characterised by the oxides mole ratio of 51.9% $(Lu_2O_3+La_2O_3+Ce_2O_3)/48.1\%SiO_2$ An ammonium carbonate water solution was added to the said mixture. Then this mixture was filtering, drain and drying. After calcination at 1400° C. the obtained oxides mixture stirred with addition of solvent and low-melting impurities, which promote an atoms diffusion through boundary of grains during a final high temperature annealing. The numerous compounds may be used as the low-melting impurities, which do not influence on an emission of $Ce^{3+}$ ions. Our investigations showed that the small additives of Li, Na, K, Cs, Be, B, F, Al, S, Cl, Zn, Sc, Ga, Ge, Se, Br, I, Sn, and In ions do not lead to decrease of light output of scintillating ceramics. A sintering aid of Mg, P, Ca, Ti, V, Cr, Mn, Fe, Co, Ni, As, Sr, Zr, Nb, Mo, Cd, Sb, Ba, Hf, Ta, W, Pb, and Bi ions decreases or completely suppresses of $Ce^{3+}$ ions emission. The sintering aid of lithium compounds, for example, LiCl, $Li_2GeF_6$, $Li_2FeO_3$, $Li_3BO_3$ promote for production of good optical quality scintillation ceramics. After removal of the trace of water and organic components, two ways of synthesis of ceramic are possible.

A first method. The oxide materials with the additives of $Li_2GeO_3$, $Li_3BO_3$ was charged into a soft platinum capsule, then the capsule was pumped in a vacuum and the hole was solder using a gas-jet. After ceramic was being synthesising in the capsule, which was placed under a massive press-form at temperature 1300° C. under 1000 atm. pressure during 2 hours.

A second method. The oxide materials with the additives of $Li_2GeO_3$, $Li_3BO_3$ was pressed under 2000 atm pressure. After that during the few hours the pressed pellets (of square or other shape) were annealed in a vacuum at temperature about 1700–1840° C. To eliminate the violet colour centers and to improve an optical quality, the pellets were annealed during 24 hours on air at temperature about 1300° C. at the final stage. In a result of these actions the scintillation ceramic products covered by thin white coat at all sides were obtained. Produced by this technique elements may be used for the X-ray computer tomography systems.

EXAMPLE 4

A scintillation substance based on a silicate comprising a lutetium (Lu) and cerium (Ce) characterised in that the composition of the substance in the form of a single crystal is represented by the chemical formula $Ce_xLu_{2+2y-x-z}A_zSi_{1-y}O_{5+y}$, where A is at least one element selected from the group consisting of Gd, Sc, Y, La, Eu, Tb, and Ca, x is a value between $1\times10^{-4}$ f.u. and 0.02 f.u., y is a value between 0.24 f.u. and 0.09 f.u., z is a value between $1\times10^{-4}$ f.u. and 0.05 f.u.

The oxide chemicals ($Lu_2O_3$, $Tb_2O_3$, $CeO_2$, $SiO_2$) with purity of 99.995% were used for the growing by Czochralski method of lutetium-terbium-cerium orthosilicate of the composition of $Ce_{0.002}Lu_{2.044}Tb_{0.03}Si_{0.962}O_{5.038}$. The crystal growth was executed from an iridium crucible of the 54 mm in diameter and 54 mm height containing the melt characterised by a mole ratio of oxides 51.9%($Ce_2O_2+Lu_2O_2+Tb_2O_3$)/48.1%$SiO_2$. The pulling rate was 2 mm/hour, rotation rate of 15 r.p.m. Crystallization was executed in a protective argon atmosphere (99.5% volume of argon with 0.5% volume of oxygen). The crystal of 55 mm length and 26 mm in diameter had a high optical quality and did not comprise the fine scattering inclusions. The polished samples from this crystal were used for the measurement of parameters are presented in TABLE 1.

The growing by Czochralski technique of lutetium-lanthanum-cerium orthosilicate of the composition of $Lu_{2.1}La_{0.02}Ce_{0.0015}Si_{0.94}O_{5.06}$ was executed from the iridium crucible of the 38 mm in diameter and 38 mm height containing the melt characterised by the oxides mole ratio of 51.9%($Ce_2O_3+Lu_2O_3+La_2O_3$)/48.1%$SiO_2$. The pulling rate was 3 mm/hour, rotation rate of 10 r.p.m. Crystallization was executed in protective argon atmosphere (99.5% volume of argon with 0.5% volume of oxygen). The crystal 17 mm in diameter and 20 mm length had the high optical quality and did not comprise the fine scattering inclusions. The polished samples from this crystal were used for measurement of parameters presented in TABLE 1. The analogous growth conditions were used for production of many samples, which parameters are presented in TABLE 1.

EXAMPLE 5

A confirmation of the invention in the particular forms of implementation for variants #2 of given invention is the scintillation substances in the form of a single crystal having the chemical formula of $Ce_xLu_{2.076-x-m-n}La_mY_nSi_{0.962}O_{5.038}$, where x is a value between $1\times10^{-4}$ f.u. and 0.02 f.u., m is a value does not exceeding 0.05 f.u., n is a value between $1\times10^{-4}$ f.u. and 2.0 f.u.

The growing by Czochralski technique of lutetium-yttrium-lantanium-cerium orthosilicate of the chemical composition of $Ce_{0.002}Lu_{1.324}Y_{0.7}La_{0.05}Si_{0.962}O_{5.038}$ was executed from the iridium crucible of the 38 mm in diameter and 38 mm height, the pulling rate was 3 mm/hour and rotation rate of 15 r.p.m. Crystallization executed from the melt characterised by the mole ratio of oxides 51.9% ($Lu_2O_3+Y_2O_3+Ce_2O_3+La_2O_3$)/48.1%$SiO_2$ in protective argon atmosphere (99.5% volume of argon with 0.5% volume of oxygen). The crystal 16 mm in diameter and 60 mm length was colourless and did not have the cracks during growth process, however the cracks appeared in the middle part of crystal boule during 24 hours cooling stage. The top of crystal did not contain the fine scattering inclusions, but the numerous scattering inclusions were in the bottom of boule. Under gamma excitation the sample from the top of crystal have demonstrated the light output about 1.3 times higher than light output of a "reference" Ce:$Lu_2SiO_5$ crystal described in EXAMPLE 1.

EXAMPLE 6

A scintillation substance containing a lithium (Li) ions, according to variants #3 and #4 of given invention, having the composition represented by the chemical formula of $Ce_xLi_{q+p}Lu_{2-p+2y-x-z}A_zSi_{1-y}O_{5+y-p}$, where A is at least one element selected from the group consisting of Gd, Sc, Y, La, Eu, and Tb, x is a value between $1\times10^{-4}$ f. units and 0.02 f. units, y is a value between 0.024 f. units and 0.09 f. units, q is q is a value between $1\times10^{-4}$ f. units and 0.2 f. units, p is a value between $1\times10^{-4}$ f. units and 0.05 f. units, z is a value does not exceeding 0.05 f. units.

To obtain the $Ce_{0.003}Li_{0.005}Lu_{2.049}La_{0.002}Si_{0.962}O_{5.038}$ crystal, the following method of making of the samples was used: the initial chemicals of lutetium oxide, silicon oxide and lithium carbonate in the quantities determined by mole relationship of oxides 51.9% ($Lu_2O_3+Li_2O+Ce_2O_3+A_2O_3$)/48.1% $SiO_2$ were thoroughly mixed, pressed in pellets and syhthesised in a platinum crucible during 10 hours at 1250° C. Then by means of induction heating the pellets were melted in an iridium crucible in a hermetically sealed chamber in protective nitrogen atmosphere (99.7% volume of nitrogen with 0.3% volume of oxygen). A cerium oxide was added into the melt before a crystal growth. The crystal 60 mm in diameter and cylindrical part of 45 mm length was grown by Kyropoulas method from the iridium crucible of the 76 mm in diameter and 78 mm height. The volume of the initial melt was equaled to 290 cm$^3$. The pull rate of crystal boule was varied from 1 mm/hr to 8 mm/hr at the different stages of growth, the rotation rate was 10 r.p.m. When the boule has grown, it was breaking off from the melt and cooled during 30 hours till room temperature. The polished samples from this boule were used for the measurements of parameters presented in TABLE 1.

The growing by Czochralski technique of the scintillation substance on the basis a lutetium-cerium orthosilicate, containing a lithium, having the chemical composition of $Ce_xLi_{0.08}Lu_{2.026-x}Si_{0.962}O_{5.008-p}$ was executed from iridium crucible of the 36 mm in diameter and 38 mm height with the pulling rate 2.7 mm/hour and rotation rate of 14 r.p.m. Crystallization was executed from the melt of composition determined by the mole ratio of oxides 51.9% ($Lu_2O_3+Ce_2O_3+Li_2O$)/48.1% $SiO_2$ in a protective argon atmosphere (99.7% volume of argon with 0.3% volume of oxygen). The crystal 19 mm in diameter and 60 mm length was colourless and did not have a cracking during growth process and in a stage of 22 hours cooling. As the top so the bottom of crystal did not contain the fine scattering inclusions except of the peripheral part of volume of the thickness about 0.5–0.7 mm. Under gamma excitation the sample from the top part of crystal demonstrated about the same value of light output as light output of a "reference" Ce:Lu$_2$SiO$_5$ crystal described in EXAMPLE 1. The same technological scheme was used for a growing and a cutting of the crystals having compositions: Ce$_x$Li$_{0.02}$Lu$_{2.072-x}$Si$_{0.962}$O$_{5.034}$, Ce$_x$Lu$_{2.036-x}$Y$_{0.04}$Si$_{0.962}$O$_{5.038}$, Ce$_x$Li$_{0.2}$Lu$_{2.006-x}$Gd$_{0.04}$Si$_{0.962}$O$_{5.018}$, Ce$_x$Li$_{0.15}$Lu$_{2.071-x-z}$Tb$_z$Si$_{0.962}$O$_{4.988}$, with a different content of cerium, x is a value between $1\times10^{-4}$ f. units and 0.02 f. units.

EXAMPLE 7

A scintillation substance according to variants #5 on the basis of a lutetium-cerium silicate containing the cation vacancies and having the composition represented by the chemical formula Ce$_x$Lu$_{9.33-x}\square_{0.67}$Si$_6$O$_{26}$ where x is a value between $1\times10^{-4}$ f. units and 0.1 f. units.

The growing by Czochralski technique of the scintillation substance on the basis of a mono-cation lutetium-cerium silicate having the chemical composition of Ce$_{0.002}$Lu$_{9.328}\square_{0.67}$Si$_6$O$_{26}$, executed from an iridium crucible of the inner diameter of 37 mm and 40 mm in height with the pulling rate of 2.7 mm/hour and rotation rate of 14 r.p.m. Crystallization was executed from the melt of stoichiometric composition in protective argon atmosphere (99.7% volume of argon with 0.3% volume of oxygen). The crystal 22 mm in diameter and 58 mm length was colourless and did not had a cracking during growth process and in a stage of 12 hours cooling. The bulk volume of crystal contained some fine scattering inclusions, the density of inclusions was increased to the bottom part of boule. The scintillation samples were made in according with technology described in EXAMPLE 1.

The same technology scheme was used for a growing and a cutting of the crystals having compositions: Ce$_{0.04}$Lu$_{9.29}\square_{0.67}$Si$_6$O$_{26}$, Ce$_{0.1}$Lu$_{9.23}\square_{0.67}$Si$_6$O$_{26}$. It is necessary to note that the increasing of cerium ions concentrated reduced a quantity of scattering inclusions.

EXAMPLE 8

A scintillation substance according to variants #5 on the basis of a lutetium-cerium silicate containing lithium and the cation vacancies and having the composition represented by the chemical formula Ce$_x$Li$_{q+p}$Lu$_{9.33-x-p}\square_{0.67}$Si$_6$O$_{26-p}$, where x is a value between $1\times10^{-4}$ f. units and 0.1 f. units, q is a value between $1\times10^{-4}$ f. units and 0.3 f. units, p is a value between $1\times10^{-4}$ f. units and 0.25 f. units.

The growth by Czochralski technique of the scintillation substance on the basis of a mono-cation lutetium-cerium silicate containing lithium and cation vacancies and having the composition represented by the chemical formula of Ce$_x$Li$_{q+p}$Lu$_{9.33-x-}\square_{0.67}$Si$_6$O$_{26-p}$, was executed from the iridium crucible of the 37 mm in diameter and 40 mm height with the pulling rate 2.7 mm/hour and rotation rate of 12 r.p.m. Crystallization was executed from the melt of stoichiometric composition in protective nitrogen atmosphere (99.7% volume of nitrogen with 0.3% volume of oxygen). The crystal 22 mm in diameter and 52 mm length was colourless and did not have a cracking during a growing and in a stage of 12 hours cooling. The bulk volume of crystal contained some amount of fine scattering inclusions. The scintillation samples were made in according with technology described in EXAMPLE 1.

The same technological scheme was used for a growing and a cutting of the crystals having the compositions: Ce$_{0.001}$Li$_{0.12}$Lu$_{9.279}\square_{0.67}$Si$_6$O$_{25.95}$, Ce$_{0.05}$Li$_{0.4}$Lu$_{9.08}\square_{0.67}$Si$_6$O$_{25.8}$.

EXAMPLE 9

A scintillation substance according to variants #7 on the basis of a lutetium-cerium silicate containing lithium and cation vacancies and having the composition represented by the chemical formula Ce$_x$Li$_{q+p}$Lu$_{9.33-x-p-z}\square_{0.67}$A$_z$Si$_6$O$_{26-p}$, where A is at least one element selected from the group consisting of Gd, Sc, Y, La, Eu, and Tb, x is a value between $1\times10^{-4}$ f. units and 0.1 f. units, q is a value between $1\times10^{-4}$ f. units and 0.3 f. units, p is a value between $1\times10^{-4}$ f. units and 0.25 f. units, z is a value between $5\times10^{-4}$ f. units and 8.9 f. units.

A growing by Czochralski technique of the scintillation substance on the basis of a mono-cation lutetium-cerium silicate containing lithium and cation vacancies and having the composition represented by the chemical formula Ce$_{0.002}$Li$_{0.2}$Lu$_{7.228-p}\square_{0.67}$La$_2$Si$_6$O$_{25.9}$ was executed from iridium crucible of the 37 mm in diameter and 40 mm height with the pulling rate of 2.7 mm/hour and rotation rate of 12 r.p.m. Crystallization was executed from the melt of stoichiometric composition in protective nitrogen atmosphere (99.8% volume of nitrogen with 0.2% volume of oxygen). The crystal 22 mm in diameter and 52 mm length diameter and 58 mm length was colourless and did not have a cracking during growth and in stage of 12 hours cooling. The bulk volume of crystal contained some fine scattering inclusions. The scintillation samples were made in according with technology described in EXAMPLE 1.

The same technology scheme was used for a growing and a cutting of the crystals having compositions: Ce$_{0.0024}$Li$_{0.2}$Lu$_{1.228-p}\square_{0.67}$Y$_8$Si$_6$O$_{25.9}$, Ce$_{0.001}$Li$_{0.1}$Lu$_{8.324}\square_{0.67}$YSi$_6$O$_{25.995}$, Ce$_{0.001}$Li$_{0.15}$Lu$_{4.279}\square_{0.67}$Gd$_5$Si$_6$O$_{25.95}$, Ce$_{0.001}$Li$_{0.35}$Lu$_{9.109}\square_{0.67}$Tb$_{0.2}$Si$_6$O$_{25.8}$, Ce$_{0.002}$Li$_{0.1}$Lu$_{0.423}\square_{0.67}$La$_{8.9}$Si$_6$O$_{25.95}$.

EXAMPLE 10

A scintillation substance according to the variants #8 and #9 on the basis of lutetium-cerium silicate containing a lithium (Li) in the quantity not a less than 1.0 f. units and having the composition represented by the chemical formula Ce$_x$Li$_{1+q+p}$Lu$_{9-x-p}$Si$_6$O$_{26-p}$, where x is a value between $1\times10^{-4}$ f. units and 0.1 f. units, q is a value in the quantity does not exceeding 0.3 f. units, p is a value in the quantity does not exceeding 0.25 f. units.

An important distinguishing technical indication of given scintillation substances is their melting point, which is a little higher than 1700° C., that is more than 300° lower than for crystals crystallised in a structural type of lutetium oxyorthosilicate. The low temperature of melting is the essential advantage for a crystal growth by Czochralski technique, because in this case the time of iridium crucibles operation is increased in tens time. There is more important a long time of usage, if the crystals growth is being carried out by Stepanov's method. An utilization of Stepanov's method opens a possibility to grow the several scintillating crystals simultaneously, for example, with size 2×2×100 mm$^3$ or the size 1×1×50 mm$^3$. It allows to eliminated the expensive stage of a cutting of a large boule into thin rods. During a cutting possibly to lost of 20%–50% of single crystal material, that considerably increases the manufacturing cost of scintillating elements for medical Micro-Positron-Emission computer Tomography (MicroPET).

In the process of growth of a profiled crystal from a melt, the crystal cross-section is determined by the form of melt column. Different physical effects are used for the shaping of a melt. A formation of a square cross-section melt column is carried out by means of an iridium former. A design of the formers and methodology of calculation of the optimal growth conditions are described in the book (P. I. Antonov, L. M. Zatulovski, A. S. Kostygov and others "An obtaining of profiled single crystals and products by Stepanov's method", L., "Nauka", 1981, page 280.).

A growing of a profiled crystal by Stepanov's method was executed from an iridium crucible equipped with the iridium former, having an outer edge cross-section of $2 \times 2$ mm$^2$, which determined the cross-section of a pulling crystal. To obtain the $Ce_{0.045}Li_{1.300}Lu_{8.905}Si_6O_{25.995}$ crystal crystallising in a hexagonal structural type, the charge of stoichiometric composition having the chemical formula $Ce_{0.045}Li_{1.300}Lu_{8.905}Si_6O_{25.995}$ was used. The following method was used for the burden preparation. The source reagents of a lithium carbonate, lutetium oxide and silicon oxide were thoroughly mixed and partially synthesised in a platinum crucible during 10 hours at 1300° C. Then, by means of induction heating the powder was melted in an iridium crucible in flow protective nitrogen atmosphere (99.7% volume of nitrogen with 0.3% volume of oxygen). A cerium oxide was added into the melt before a crystal growth. The former allowed to grow from one to nine profiled crystals simultaneously. Seeding was fulfilled onto the crystal obtained by Czochralski technique. A seed crystal was cut along a crystallographic direction of the axis of six order. The profiled crystals were pulled out of melt at a speed of 3–20 mm/hour without rotation. Upon the crystal reaching the length of 50 mm they were broken away from the former by a sharp increasing of the pulling speed and 30 minutes later they were being extracted from installation.

The profiled crystal rods were cut into the few scintillating elements with sizes $2 \times 2 \times 10$ mm$^3$. The polished samples of $Ce_{0.045}Li_{1.300}Lu_{8.905}Si_6O_{25.995}$ crystal were used for measurements of parameters presented in TABLE 1.

The same technological scheme was used for a growing and a cutting of the crystals having the compositions: $Ce_{0.001}LiLu_{8.998}$ $Si_6O_{26}$, $Ce_{0.04}LiLu_{8.96}Si_6O_{26}$, $Ce_{0.1}LiLu_{8.9}Si_6$ $O_{26}$, $Ce_{0.002}Li_{1.45}Lu_{8.798-p}Si_6O_{25.8}$, $Ce_{0.0015}Li_{1.3}Lu_{8.8985-p}Si_6O_{25.9}$.

EXAMPLE 11

A scintillation substance according to variant #10 on the basis of silicate containing a lutetium (Lu) and cerium (Ce) and characterised in that it contains a lithium Li in the quantity exceeding 1.0 f.u. and its composition is represented by the chemical formula $Ce_xLi_{1+q+p}Lu_{9-x-p-z}A_zSi_6O_{26-p}$, where A is at least one element selected from the group consisting of Gd, Sc, Y, La, Eu, and Tb, x is a value between $1 \times 10^{-4}$ f. units and 0.1 f. units, q is a value between $1 \times 10^{-4}$ f. units and 0.3 f. units, p is a value between $1 \times 10^{-4}$ f. units and 0.25 f. units, z is a value between $5 \times 10^{-4}$ f.u. and 8.9 f. units.

To obtain a scintillation substance of composition of $Ce_{0.045}Li_{1.1}Lu_{0.08}La_{0.02}Y_{8.755}Si_6O_{26}$ crystallising in a hexagonal syngony, the charge of stoichiometric composition having the chemical formula of $Ce_{0.045}Li_{1.1}Lu_{0.08}La_{0.02}Gd_{8.755}Si_6O_{26}$ was used. A growing of crystal was executed from an iridium crucible of the 40 mm in diameter in a protective atmosphere (99.5% volume of nitrogen with 0.5% volume of oxygen), the pulling rates were 5 mm/hour and 10 mm/hour and rotation rate was 11 r.p.m. in these growth conditions the crystal approximately 35 mm length and 18 mm in diameter was grown, the boule had a white-yellow colour and did not have the fine scattering inclusions even at the 10 mm/hour pulling rate. The polished sample of this crystal under gamma excitation demonstrated the light output about 10 time lower than a light output of a "reference" $Ce:Lu_2SiO_5$ crystal, a technology of fabrication of which is described in EXAMPLE 1. On the basis of this an upper limit of substitution of lutetium ions by other elements in the substances of variant #10 having the chemical formula of $Ce_xLi_{1+q+p}Lu_{9-x-p-z}A_zSi_6O_{26-p}$ was set at the value of z=8.9 f. units. In this case the crystals have a significantly lower density and light output, however the cost of charged reagents, and, therefore, a manufacturing cost of scintillation crystals are being decreased appreciably. Such crystals are being interested for utilization in the sensors, for which the more important parameter is a low price and a high resistance of scintillator to the outside exposure, such as a high temperature, a big humidity, a very high level of radiation, which may destroy, for example, a gamma dosimeter.

The same technological scheme was used for a growing of crystals having the compositions: $Ce_{0.001}Li_{1.2}Lu_{3.898}Gd_{5.1}Si_6O_{26}$, $Ce_{0.04}Li_{1.2}Lu_{8.66}Eu_{0.2}Si_6O_{25.9}$, $Ce_{0.1}Li_{1.2}Lu_{7.9}Sc_{0.8}Si_6O_{25.8}$, $Ce_{0.002}Li_{1.45}Lu_{6.298}Y_{2.5}Si_6O_{25.8}$, $Ce_{0.0015}Li_{1.3}Lu_{8.3985}La_{0.5}Si_6O_{25.9}$.

While the foregoing description represent the preferred embodiments of the present invention, it will be understood that various additions and/or substitutions may be made therein without departing from the spirit and scope of the present invention. One skilled in the art will appreciate that the invention may be used with many modifications of structure, forms, arrangement, proportions, materials, and components and otherwise, used in the practice of the invention and which are particularly adapted to specific environments and operative requirements, without departing from the principles of the present invention. The presently disclosed embodiments are therefore to be considered in all respects as illustrative and not restrictive.

We claim:

1. A scintillation substance based on a silicate comprising a lutetium (Lu) and cerium (Ce) characterized in that the composition of the substance is represented by the chemical formula $Ce_xLu_{2+2y-x}Si_{1-y}O_{5+y}$, x is a value between $1 \times 10^{-4}$ f.u. and 0.02 f.u., y is a value between 0.024 f.u. and 0.09 f.u.

2. A scintillation substance according to claim 1, characterised in that the composition of the substance in the form of a single crystal is represented by the chemical formula $Ce_xLu_{2.076-x}Si_{0.962}O_{5.038}$, x is a value between $1 \times 10^{-4}$ f.u. and 0.02 f.u.

3. A method of making the scintillating substance according to claim 1, characterised in that a single crystal is being grown by a directional crystallization method from a melt made from the charge of the composition defined by mole ratio of oxides 51.9% $(Lu_2O_3+Ce_2O_3)/48.1\%$ $SiO_2$.

4. A method of making the scintillating substance according to claim 1, characterised in that a single crystal is being grown by Czochralski method from a melt made from the charge of the composition defined by mole ratio of oxides 51.9% $(Lu_2O_3+Ce_2O_3)/48.1\%$ $SiO_2$.

5. A scintillation substance based on a silicate comprising a lutetium (Lu) and cerium (Ce) characterised in that the composition of the substance in the form of a single crystal is represented by the chemical formula $$Ce_xLu_{2+2y-x-z}A_zSi_{1-y}O_{5+y},$$

where A is at least one element selected from the group consisting of Gd, Sc, Y, La, Eu, Tb, and Ca,
x is a value between $1\times10^{-4}$ f.u. and 0.02 f.u.,
y is a value between 0.024 f.u. and 0.09 f.u.,
z is a value between $1\times10^{-4}$ f.u. and 0.05 f.u.

6. The scintillation substance according to claim 5, characterised in that the composition of the substance in the form of a single crystal is represented by the chemical formula $$Ce_xLu_{2.076-x-z}A_zSi_{0.962}O_{5.038},$$

where A is at least one element selected from the group consisting of Gd, Sc, Y, La, Eu, Tb, and Ca,
x is a value between $1\times10^{-4}$ f.u. and 0.02 f.u.,
z is a value between $1\times10^{-4}$ f.u. and 0.05 f.u.

7. The scintillation substance according to claim 5, characterised in that the composition of the substance in the form of a single crystal is represented by the chemical formula $$Ce_xLu_{2.076-x-m-n}La_mY_nSi_{0.962}O_{5.038},$$

x is a value between $1\times10^{-4}$ f.u. and 0.02 f.u.,
m is a value does not exceeding 0.05 f.u.,
n is a value between $1\times10^{-4}$ f.u. and 2.0 f.u.

8. A method of making the scintillating substance according to claim 5, characterised in that a single crystal is being grown by a directional crystallization method from a melt made from the charge of the composition defined by mole ratio of oxides 51.9% $(Lu_2O_3+A_2O_3+Ce_2O_3)/48.1\%$ $SiO_2$, where A is at least one element selected from the group consisting of Gd, Sc, Y, La, Eu, Tb, and Ca.

9. A method of making the scintillating substance according to claim 5, characterised in that an oversized crystal is being grown by Kyropoulos method from a melt made from the charge of the composition defined by mole ration of oxides 51.9% $(Lu_2O_3+A_2O_3+Ce_2O_3)/48.1\%$ $SiO_2$, where A is at least one element selected from the group consisting of Gd, Sc, Y, La, Eu, Tb, and Ca.

10. A scintillation substance based on a silicate comprising lutetium (Lu) and cerium (Ce) characterised in that it contains a lithium Li in a quantity that does not exceed 0.25 f.u. and its composition is represented by the chemical formula $$Ce_xLi_{q+p}Lu_{2-p+2y-x}Si_{1-y}O_{5+y-p}$$

x is a value between $1\times10^{-4}$ f.u. and 0.02 f.u.,
y is a value between 0.024 f.u. and 0.09 f.u.,
q is a value between $1\times10^{-4}$ f.u. and 0.02 f.u.,
p is a value between $1\times10^{-4}$ f.u. and 0.05 f.u.

11. A scintillation substance according to claim 10, characterised in that the composition of the substance in the form of a single crystal containing lithium Li in a quantity that does not exceed 0.25 f.u. and is represented by the chemical formula $$Ce_xLi_{q+p}Lu_{2.076-p-x}Si_{0.962}O_{5.038-p},$$

x is a value between $1\times10^{-4}$ f.u. and 0.02 f.u.,
q is a value between $1\times10^{-4}$ f.u. and 0.2 f.u.,
p is a value between $1\times10^{-4}$ f.u. and 0.05 f.u.

12. A method of making the scintillating substance according to claim 10, characterised in that a single crystal is being grown by a directional crystallization method from a melt made from the charge of the composition defined by mole ratio of oxides 51.9% $(Lu_2O_3+Li_2O+Ce_2O_3)/48.1\%$ $SiO_2$.

13. A scintillation substance based on a silicate comprising lutetium (Lu) and cerium (Ce) characterised in that it contains a lithium Li in a quantity that does not exceed 0.25 f.u. and its composition is represented by the chemical formula $$Ce_xLi_{q+p}Lu_{2-p+2y-x-z}A_zSi_{1-y}O_{5+y-p},$$

where A is at least one element selected from the group consisting of Gd, Sc, Y, La, Eu, and Tb,
x is a value between $1\times10^{-4}$ f.u. and 0.02 f.u.,
y is a value between 0.024 f.u. and 0.09 f.u.,
z is a value between $1\times10^{-4}$ f.u. and 0.05 f.u.,
q is a value between $1\times10^{-4}$ f.u. and 0.2 f.u.,
p is a value between $1\times10^{-4}$ f.u. and 0.05 f.u.

14. The scintillation substance according to claim 13, characterised in that the composition of the substance in the form of a single crystal containing lithium Li in a quantity that does not exceed 0.25 f.u. and is represented by the chemical formula $$Ce_xLi_{q+p}Lu_{2.076-p-x-z}A_zSi_{0.962}O_{5.038-p},$$

where A is at least one element selected from the group consisting of Gd, Sc, Y, La, Eu, and Tb,
x is a value between $1\times10^{-4}$ f.u. and 0.02 f.u.,
z is a value between $1\times10^{-4}$ f.u. and 0.05 f.u.,
q is a value between $1\times10^{-4}$ f.u. and 0.2 f.u.,
p is a value between $1\times10^{-4}$ f.u. and 0.05 f.u.

15. A method of making the scintillating substance according to claim 13, characterised in that a single crystal is being grown by a directional crystallization method from a melt made from the charge of the composition defined by mole ratio of oxides 51.9% $(Lu_2O_3+Li_2O+A_2O_3+Ce_2O_3)/48.1\%$ $SiO_2$.

16. A scintillation substance based on a silicate comprising lutetium (Lu) and cerium (Ce) characterised in that it contains lithium Li and its composition is represented by the chemical formula $$Ce_xLi_{q+p}Lu_{9.33-x-p}\square_{0.67}Si_6O_{26-p},$$

x is a value between $1\times10^{-4}$ f.u. and 0.1 f.u.,
q is a value between $1\times10^{-4}$ f.u. and 0.3 f.u.,
p is a value between $1\times10^{-4}$ f.u. and 0.25 f.u.

17. A scintillation substance based on a silicate comprising lutetium (Lu) and cerium (Ce) characterised in that it contains lithium Li and its composition is represented by the chemical formula $$Ce_xLi_{q+p}Lu_{9.33-x-p-z}\square_{0.67}A_zSi_6O_{26-p},$$

where A is at least one element selected from the group consisting of Gd, Sc, Y, La, Eu, and Tb,
x is a value between $1\times10^{-4}$ f.u. and 0.1 f.u.,
q is a value between $1\times10^{-4}$ f.u. and 0.3 f.u.,
p is a value between $1\times10^{-4}$ f.u. and 0.25 f.u.,
z is a value between $5\times10^{-4}$ f.u. and 8.9 f.u.

18. A scintillation substance based on a silicate comprising lutetium (Lu) and cerium (Ce) characterised in that it contains lithium Li and its composition is represented by the chemical formula $$Ce_xLiLu_{9-x}Si_6O_{26},$$

x is a value between $1\times10^{-4}$ f.u. and 0.1 f.u.

19. A scintillation substance based on a silicate comprising lutetium (Lu) and cerium (Ce) characterised in that it contains lithium Li in a quantity exceeding 1.0 f.u. and its composition is represented by the chemical formula $$Ce_xLi_{1+q+p}Lu_{9-x-p}Si_6O_{26-p},$$

x is a value between $1\times10^{-4}$ f.u. and 0.1 f.u.,
q is a value between $1\times10^{-4}$ f.u. and 0.3 f.u.,
p is a value between $1\times10^{-4}$ f.u. and 0.25 f.u.

20. A scintillation substance based on a silicate comprising lutetium (Lu) and cerium (Ce) characterised in that it contains lithium Li in a quantity exceeding 1.0 f.u. and its composition is represented by the chemical formula $$Ce_xLi_{1+q+p}Lu_{9-x-p-z}A_zSi_6O_{26-p},$$

where A is at least one element selected from the group consisting of Gd, Sc, Y, La, Eu, and Tb,
x is a value between $1\times10^{-4}$ f.u. and 0.1 f.u.,
q is a value between $1\times10^{-4}$ f.u. and 0.3 f.u.,
p is a value between $1\times10^{-4}$ f.u. and 0.25 f.u.,
z is a value between $5\times10^{-4}$ f.u. and 8.9 f.u.

* * * * *

UNITED STATES PATENT AND TRADEMARK OFFICE
CERTIFICATE OF CORRECTION

PATENT NO. : 7,132,060 B2  Page 1 of 1
APPLICATION NO. : 10/502960
DATED : November 7, 2006
INVENTOR(S) : Alexander Zagumennyi et al.

It is certified that error appears in the above-identified patent and that said Letters Patent is hereby corrected as shown below:

Title page, item [62] insert

--Related U.S. Application Data

This application claims priority to PCT Application No. PCT/RU2004/000094 filed on March 12, 2004, which application claims the benefit of Russian Patent Application No. 2003132127 filed on November 4, 2003, both of which are incorporated herein by reference in their entireties for all purpose.--

Signed and Sealed this
Twenty-first Day of February, 2012

David J. Kappos
*Director of the United States Patent and Trademark Office*

UNITED STATES PATENT AND TRADEMARK OFFICE
CERTIFICATE OF CORRECTION

PATENT NO. : 7,132,060 B2
APPLICATION NO. : 10/502960
DATED : November 7, 2006
INVENTOR(S) : Alexander Zagumennyi et al.

It is certified that error appears in the above-identified patent and that said Letters Patent is hereby corrected as shown below:

In the Claims

Column 34, line 45, Claim 1 should read as follows:

--1. A scintillation substance based on a silicate comprising lutetium (Lu) and cerium (Ce) characterized in that the composition of the substance is represented by the chemical formula
   $Ce_xLu_{2+2y-x}Si_{1-y}O_{5+y}$,
x is a value between $1 \times 10^{-4}$ f.u. and 0.02 f.u.,
y is a value between 0.024 f.u. and 0.09 f.u.--

Column 35, lines 2-12, Claim 5 should read as follows:

--5. A scintillation substance based on a silicate comprising lutetium (Lu) and cerium (Ce) characterized in that the composition of the substance in the form of a single crystal is represented by the chemical formula
   $Ce_xLu_{2+2y-x-z}A_zSi_{1-y}O_{5+y}$,
where A is at least one element selected from the group consisting of Gd, Sc, Y, La, Eu, Tb, Ca,
   x is a value between $1 \times 10^{-4}$ f.u. and 0.02 f.u.,
   y is a value between 0.024 f.u. and 0.09 f.u.,
   z is a value between $1 \times 10^{-4}$ f.u. and 0.05 f.u.--

Signed and Sealed this
Second Day of September, 2014

Michelle K. Lee
*Deputy Director of the United States Patent and Trademark Office*